US012329943B2

(12) United States Patent
Tan-Malecki et al.

(10) Patent No.: US 12,329,943 B2
(45) Date of Patent: *Jun. 17, 2025

(54) INJECTOR AND METHOD OF ASSEMBLY

(71) Applicant: AMGEN INC., Thousand Oaks, CA (US)

(72) Inventors: Francisca Tan-Malecki, Westlake Village, CA (US); Ronald Forster, Simi Valley, CA (US); Scott M. Nunn, San Mateo, CA (US); Mark D. Holt, Moorpark, CA (US); Son C. Tran, San Francisco, CA (US); Sheldon Moberg, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 600 days.

This patent is subject to a terminal disclaimer.

(21) Appl. No.: 17/590,175

(22) Filed: Feb. 1, 2022

(65) Prior Publication Data

US 2022/0152308 A1    May 19, 2022

Related U.S. Application Data

(63) Continuation of application No. 17/350,883, filed on Jun. 17, 2021, now Pat. No. 11,273,260, which is a
(Continued)

(51) Int. Cl.
*A61M 5/31* (2006.01)
*A61M 5/145* (2006.01)
(Continued)

(52) U.S. Cl.
CPC ............ *A61M 5/31* (2013.01); *A61M 5/1452* (2013.01); *A61M 5/148* (2013.01); *A61M 5/158* (2013.01);
(Continued)

(58) Field of Classification Search
CPC .. A61M 5/162; A61M 5/2455; A61M 5/2466; A61M 2005/2474;
(Continued)

(56) References Cited

U.S. PATENT DOCUMENTS 2,371,086 A    3/1945 Watson et al.
2,591,706 A    4/1952 Lockhart
(Continued)

FOREIGN PATENT DOCUMENTS

AT       404556 B       12/1998
CA       2779793 A1     5/2011
(Continued)

OTHER PUBLICATIONS

European Patent Application No. 20187706.5, Communication Pursuant to Article 94(3) EPC, dated May 3, 2023.
(Continued)

*Primary Examiner* — Nilay J Shah
(74) *Attorney, Agent, or Firm* — MARSHALL, GERSTEIN & BORUN LLP

(57) ABSTRACT

An injector may include a container having a wall with an interior surface and a seal assembly with an interior surface, the interior surfaces of the wall and the seal assembly defining a closed sterile reservoir filled with a drug product. The injector may also include a fluid delivery system comprising a clean, unsheathed, rigid container needle having a point disposed only partially through the seal assembly in a storage state, and disposed through the interior surface of the seal assembly into the sterile reservoir in a delivery state. Further, the injection may include an actuator that is adapted to move the container needle from the storage state to the delivery state.

20 Claims, 6 Drawing Sheets

Related U.S. Application Data continuation of application No. 16/687,254, filed on Nov. 18, 2019, now Pat. No. 11,058,821, which is a continuation of application No. 15/040,308, filed on Feb. 10, 2016, now Pat. No. 10,537,681, which is a continuation of application No. 14/350,687, filed as application No. PCT/US2012/059680 on Oct. 11, 2012, now Pat. No. 9,987,428.

(60) Provisional application No. 61/547,667, filed on Oct. 14, 2011.

(51) Int. Cl.

| | | |
|---|---|---|
| A61M 5/148 | (2006.01) | |
| A61M 5/158 | (2006.01) | |
| A61M 5/162 | (2006.01) | |
| A61M 5/172 | (2006.01) | |
| A61M 5/24 | (2006.01) | |
| B65B 3/00 | (2006.01) | |
| B65B 7/28 | (2006.01) | |
| B65B 55/08 | (2006.01) | |
| B65B 55/10 | (2006.01) | |
| A61M 5/142 | (2006.01) | |

(52) U.S. Cl.
CPC .......... *A61M 5/162* (2013.01); *A61M 5/1626* (2013.01); *A61M 5/172* (2013.01); *A61M 5/2466* (2013.01); *B65B 3/003* (2013.01); *B65B 7/2821* (2013.01); *B65B 55/08* (2013.01); *B65B 55/10* (2013.01); *A61M 5/14244* (2013.01); *A61M 5/2455* (2013.01); *A61M 2005/247* (2013.01); *A61M 2005/2474* (2013.01); *A61M 2005/3114* (2013.01); *A61M 2207/00* (2013.01)

(58) Field of Classification Search
CPC .... A61M 2005/247; A61M 2005/3206; A61M 5/34; A61M 5/343; A61M 5/24; A61M 5/178

See application file for complete search history.

(56) References Cited

U.S. PATENT DOCUMENTS

| | | |
|---|---|---|
| 2,677,373 A | 5/1954 | Barradas |
| 2,688,967 A | 9/1954 | Huber |
| 2,842,126 A | 7/1958 | Brown |
| 3,187,749 A | 6/1965 | Sarnoff |
| 3,336,924 A | 8/1967 | Sarnoff et al. |
| 3,342,180 A | 9/1967 | Sandhage |
| 3,368,557 A | 2/1968 | Hassing et al. |
| 3,368,558 A | 2/1968 | Sarnoff et al. |
| 3,376,866 A | 4/1968 | Ogle |
| 3,557,787 A | 1/1971 | Cohen |
| 3,605,744 A | 9/1971 | Dwyer |
| 3,640,278 A | 2/1972 | Friedman |
| 3,662,753 A | 5/1972 | Tassell |
| 3,682,174 A | 8/1972 | Cohen |
| 3,739,779 A | 6/1973 | Pfleger |
| 3,739,947 A | 6/1973 | Baumann et al. |
| 3,757,779 A | 9/1973 | Rovinski |
| 3,785,379 A | 1/1974 | Cohen |
| 3,825,003 A | 7/1974 | Kruck |
| 3,835,855 A | 9/1974 | Barr, Jr. |
| 3,872,864 A | 3/1975 | Allen, Jr. |
| 3,872,867 A | 3/1975 | Killinger |
| 3,916,893 A | 11/1975 | De Felice |
| 3,967,621 A | 7/1976 | Schwarz |
| 3,995,630 A | 12/1976 | van de Veerdonk |
| 4,055,177 A | 10/1977 | Cohen |
| 4,178,930 A | 12/1979 | Fisher, Jr. |
| 4,188,949 A | 2/1980 | Antoshkiw |
| 4,196,732 A | 4/1980 | Wardlaw |
| 4,215,689 A | 8/1980 | Akiyama et al. |
| 4,281,653 A | 8/1981 | Barta et al. |
| 4,296,786 A | 10/1981 | Brignola |
| 4,411,163 A | 10/1983 | White |
| 4,523,679 A | 6/1985 | Paikoff et al. |
| 4,576,211 A | 3/1986 | Valentini et al. |
| 4,619,651 A | 10/1986 | Kopfer et al. |
| 4,626,244 A | 12/1986 | Reinicke |
| 4,632,672 A | 12/1986 | Kvitrud |
| 4,655,747 A | 4/1987 | Allen, Jr. |
| 4,753,638 A | 6/1988 | Peters |
| 4,784,156 A | 11/1988 | Garg |
| 4,834,714 A | 5/1989 | Lascar et al. |
| 4,838,857 A | 6/1989 | Strowe et al. |
| 4,883,473 A | 11/1989 | Thomas |
| 4,915,690 A | 4/1990 | Cone et al. |
| 4,919,658 A * | 4/1990 | Badia .................. A61M 5/162 604/199 |
| 5,019,047 A | 5/1991 | Kriesel |
| 5,078,691 A | 1/1992 | Hamacher |
| 5,135,489 A | 8/1992 | Jepson et al. |
| 5,147,328 A | 9/1992 | Dragosits et al. |
| 5,205,820 A | 4/1993 | Kriesel |
| 5,267,974 A | 12/1993 | Lambert |
| 5,312,336 A | 5/1994 | Haber et al. |
| 5,334,197 A | 8/1994 | Kriesel et al. |
| 5,358,491 A | 10/1994 | Johnson et al. |
| 5,364,369 A | 11/1994 | Reynolds et al. |
| 5,441,490 A | 8/1995 | Svedman |
| 5,480,386 A | 1/1996 | Brohy et al. |
| 5,496,284 A | 3/1996 | Waldenburg |
| 5,593,391 A | 1/1997 | Stanners |
| 5,618,269 A | 4/1997 | Jacobsen et al. |
| 5,620,425 A | 4/1997 | Heffernan et al. |
| 5,643,206 A | 7/1997 | Fischer |
| 5,693,018 A | 12/1997 | Kriesel et al. |
| 5,713,866 A | 2/1998 | Wilmot |
| 5,749,857 A | 5/1998 | Cuppy |
| 5,807,323 A | 9/1998 | Kriesel et al. |
| 5,865,744 A | 2/1999 | Lemelson |
| 5,885,250 A | 3/1999 | Kriesel et al. |
| 5,921,962 A | 7/1999 | Kriesel et al. |
| 5,957,891 A | 9/1999 | Kriesel et al. |
| 5,957,895 A | 9/1999 | Sage et al. |
| 5,957,896 A | 9/1999 | Bendek et al. |
| 5,962,794 A | 10/1999 | Kriesel et al. |
| 6,027,482 A | 2/2000 | Imbert |
| 6,065,270 A | 5/2000 | Reinhard et al. |
| 6,068,613 A | 5/2000 | Kriesel et al. |
| 6,159,180 A | 12/2000 | Kriesel et al. |
| 6,189,292 B1 | 2/2001 | Odell et al. |
| 6,221,055 B1 | 4/2001 | Shaw et al. |
| 6,248,095 B1 | 6/2001 | Giambattista et al. |
| 6,355,019 B1 | 3/2002 | Kriesel et al. |
| 6,482,176 B1 | 11/2002 | Wich |
| 6,491,665 B1 | 12/2002 | Vetter et al. |
| 6,491,667 B1 | 12/2002 | Keane et al. |
| 6,537,249 B2 | 3/2003 | Kriesell et al. |
| 6,589,229 B1 | 7/2003 | Connelly et al. |
| 6,595,956 B1 | 7/2003 | Gross et al. |
| 6,793,646 B1 | 9/2004 | Giambattista et al. |
| 6,824,529 B2 | 11/2004 | Gross et al. |
| 6,883,222 B2 | 4/2005 | Landau |
| 7,033,343 B2 | 4/2006 | McWethy et al. |
| 7,063,684 B2 | 6/2006 | Moberg |
| 7,112,188 B2 | 9/2006 | Waldenburg |
| 7,169,132 B2 | 1/2007 | Bendek et al. |
| 7,220,245 B2 | 5/2007 | Kriesel |
| 7,250,037 B2 | 7/2007 | Shermer et al. |
| 7,402,150 B2 | 7/2008 | Matsumoto et al. |
| 7,475,797 B2 | 1/2009 | Kim |
| 7,524,300 B2 | 4/2009 | Patton |
| 7,608,055 B2 | 10/2009 | Griffiths et al. |
| 7,628,782 B2 | 12/2009 | Adair et al. |
| 7,641,649 B2 | 1/2010 | Moberg et al. |
| 7,686,787 B2 | 3/2010 | Moberg et al. |
| 7,704,228 B2 | 4/2010 | Patton |
| 7,731,680 B2 | 6/2010 | Patton |

(56) References Cited

U.S. PATENT DOCUMENTS

| | | |
|---|---|---|
| 7,744,589 B2 | 6/2010 | Mounce et al. |
| 7,749,190 B2 | 7/2010 | Griffiths et al. |
| 7,776,030 B2 | 8/2010 | Estes et al. |
| 7,789,853 B2 | 9/2010 | Kriesel |
| 7,789,857 B2 | 9/2010 | Moberg et al. |
| 7,828,772 B2 | 11/2010 | Kriesel et al. |
| 7,832,078 B2 | 11/2010 | Thilly et al. |
| 7,837,653 B2 | 11/2010 | Kriesel et al. |
| 7,879,026 B2 | 2/2011 | Estes et al. |
| 7,905,868 B2 | 3/2011 | Moberg et al. |
| 7,935,087 B2 | 5/2011 | Judd et al. |
| 7,935,105 B2 | 5/2011 | Miller et al. |
| 7,938,801 B2 | 5/2011 | Hawkins et al. |
| 7,955,305 B2 | 6/2011 | Moberg et al. |
| 7,963,956 B2 | 6/2011 | Kunst |
| 7,967,034 B2 * | 6/2011 | Py ........................ A61J 1/2096 141/69 |
| 8,021,333 B2 | 9/2011 | Kaal et al. |
| 8,025,658 B2 | 9/2011 | Chong et al. |
| 8,029,468 B2 | 10/2011 | Kriesel et al. |
| 8,030,457 B2 | 10/2011 | Jackson et al. |
| 8,032,226 B2 | 10/2011 | Miller et al. |
| 8,062,253 B2 | 11/2011 | Nielsen et al. |
| 8,105,279 B2 | 1/2012 | Mernoe et al. |
| 8,142,398 B1 | 3/2012 | Kriesel |
| 8,177,775 B2 | 5/2012 | Kunst |
| 8,292,848 B2 | 10/2012 | Kriesel et al. |
| 8,303,535 B2 | 11/2012 | Both et al. |
| 8,328,449 B2 | 12/2012 | Wightman et al. |
| 8,353,866 B2 | 1/2013 | Evans, Jr. |
| 8,372,035 B2 | 2/2013 | Matusch |
| 8,409,142 B2 | 4/2013 | Causey et al. |
| 8,454,562 B1 | 6/2013 | Sims |
| 8,568,367 B2 | 10/2013 | Griffiths et al. |
| 8,597,256 B2 | 12/2013 | Lanin et al. |
| 8,603,034 B2 | 12/2013 | Lynch et al. |
| 8,647,302 B2 | 2/2014 | Briones et al. |
| 8,684,968 B2 | 4/2014 | Genosar |
| 8,728,024 B2 | 5/2014 | Kamen et al. |
| 8,905,974 B2 | 12/2014 | Carter et al. |
| 8,961,467 B2 | 2/2015 | Lanigan et al. |
| 9,125,981 B2 | 9/2015 | Mann et al. |
| 9,205,194 B2 | 12/2015 | Mojdehbakhsh et al. |
| 9,987,428 B2 | 6/2018 | Tan-Malecki et al. |
| 10,314,976 B2 | 6/2019 | Tan-Malecki et al. |
| 10,537,681 B2 | 1/2020 | Tan-Malecki et al. |
| 10,537,682 B2 | 1/2020 | Tan-Malecki et al. |
| 10,850,037 B2 | 12/2020 | Gibson |
| 11,097,055 B2 | 8/2021 | Gibson |
| 11,110,225 B2 | 9/2021 | Tan-Malecki et al. |
| 11,160,931 B2 | 11/2021 | Tan-Malecki et al. |
| 2002/0123719 A1 * | 9/2002 | Lavi ........................ A61M 5/19 604/82 |
| 2002/0139088 A1 | 10/2002 | Woodworth et al. |
| 2002/0173753 A1 | 11/2002 | Caizza et al. |
| 2003/0055380 A1 | 3/2003 | Flaherty |
| 2003/0132547 A1 | 7/2003 | Heffernan et al. |
| 2003/0191291 A1 | 10/2003 | Kochendoerfer et al. |
| 2003/0212362 A1 | 11/2003 | Roser |
| 2004/0010207 A1 | 1/2004 | Flaherty et al. |
| 2004/0015135 A1 | 1/2004 | Wilkinson |
| 2004/0074076 A1 | 4/2004 | Landau |
| 2004/0092865 A1 | 5/2004 | Flaherty et al. |
| 2004/0092878 A1 | 5/2004 | Flaherty |
| 2004/0133159 A1 | 7/2004 | Haider et al. |
| 2004/0236273 A1 | 11/2004 | Tanaka et al. |
| 2005/0113763 A1 | 5/2005 | Reynolds |
| 2005/0154357 A1 | 7/2005 | Pinel |
| 2005/0177108 A1 | 8/2005 | Paul et al. |
| 2005/0267422 A1 | 12/2005 | Kriesel |
| 2005/0277883 A1 | 12/2005 | Kriesel |
| 2006/0178644 A1 | 8/2006 | Reynolds |
| 2006/0191594 A1 | 8/2006 | Py |
| 2006/0217659 A1 | 9/2006 | Patton |
| 2006/0264900 A1 | 11/2006 | Patton |
| 2006/0264901 A1 | 11/2006 | Patton |
| 2007/0049875 A1 | 3/2007 | Patton |
| 2007/0060877 A1 | 3/2007 | Bassarab et al. |
| 2007/0100294 A1 | 5/2007 | Sugita et al. |
| 2007/0186510 A1 | 8/2007 | Wittland et al. |
| 2007/0276338 A1 | 11/2007 | Shue et al. |
| 2007/0282269 A1 | 12/2007 | Carter et al. |
| 2008/0009835 A1 | 1/2008 | Kriesel et al. |
| 2008/0051711 A1 | 2/2008 | Mounce et al. |
| 2008/0097306 A1 | 4/2008 | Smith et al. |
| 2008/0140019 A1 | 6/2008 | Thilly et al. |
| 2008/0154243 A1 | 6/2008 | Krumme |
| 2008/0172034 A1 | 7/2008 | Patton |
| 2008/0183140 A1 | 7/2008 | Paproski et al. |
| 2008/0215004 A1 | 9/2008 | Harding et al. |
| 2008/0215035 A1 | 9/2008 | Yodfat et al. |
| 2008/0243084 A1 | 10/2008 | DeStefano et al. |
| 2008/0243085 A1 | 10/2008 | DeStefano |
| 2008/0269681 A1 | 10/2008 | Kavazov et al. |
| 2008/0319385 A1 | 12/2008 | Kriesel et al. |
| 2009/0024083 A1 | 1/2009 | Kriesel et al. |
| 2009/0099522 A1 | 4/2009 | Kamen et al. |
| 2009/0192471 A1 | 7/2009 | Carter et al. |
| 2009/0259209 A1 | 10/2009 | Chong et al. |
| 2009/0270811 A1 | 10/2009 | Mounce et al. |
| 2009/0275888 A1 | 11/2009 | Kriesel et al. |
| 2009/0299277 A1 | 12/2009 | Kamen et al. |
| 2010/0010472 A1 | 1/2010 | Moore |
| 2010/0047914 A1 | 2/2010 | Peyman et al. |
| 2010/0049128 A1 | 2/2010 | McKenzie et al. |
| 2010/0082010 A1 | 4/2010 | Adair et al. |
| 2010/0140125 A1 | 6/2010 | Mathiasen et al. |
| 2010/0173024 A1 | 7/2010 | McDaniel |
| 2010/0179473 A1 | 7/2010 | Genosar |
| 2010/0198182 A1 | 8/2010 | Lanigan et al. |
| 2010/0198183 A1 | 8/2010 | Lanigan et al. |
| 2010/0217242 A1 | 8/2010 | Mann et al. |
| 2010/0239654 A1 | 9/2010 | Winter |
| 2010/0249753 A1 | 9/2010 | Gaisser et al. |
| 2010/0298811 A1 | 11/2010 | Connair |
| 2011/0004188 A1 | 1/2011 | Shekalim |
| 2011/0022002 A1 | 1/2011 | Hanson et al. |
| 2011/0054390 A1 | 3/2011 | Searle et al. |
| 2011/0092904 A1 | 4/2011 | Kriesel et al. |
| 2011/0097318 A1 | 4/2011 | Gadgil |
| 2011/0112484 A1 | 5/2011 | Carter et al. |
| 2011/0112501 A1 | 5/2011 | Garfield et al. |
| 2011/0112504 A1 | 5/2011 | Causey et al. |
| 2011/0137294 A1 | 6/2011 | Calimeri et al. |
| 2011/0160696 A1 | 6/2011 | Hoss |
| 2011/0166512 A1 | 7/2011 | Both et al. |
| 2011/0190694 A1 | 8/2011 | Lanier, Jr. et al. |
| 2011/0202004 A1 | 8/2011 | Miller et al. |
| 2011/0224640 A1 | 9/2011 | Kuhn et al. |
| 2011/0245773 A1 | 10/2011 | Estes et al. |
| 2011/0282300 A1 | 11/2011 | Kriesel et al. |
| 2012/0010594 A1 | 1/2012 | Holt et al. |
| 2012/0022499 A1 | 1/2012 | Anderson et al. |
| 2012/0029440 A1 | 2/2012 | Boyd et al. |
| 2012/0083738 A1 | 4/2012 | Grant et al. |
| 2012/0123384 A1 | 5/2012 | Mernoe et al. |
| 2012/0130318 A1 | 5/2012 | Young |
| 2012/0143144 A1 | 6/2012 | Young |
| 2012/0179109 A1 | 7/2012 | Takemoto et al. |
| 2012/0191060 A1 | 7/2012 | Banister et al. |
| 2012/0191074 A1 | 7/2012 | Steinbach |
| 2012/0209197 A1 | 8/2012 | Lanigan et al. |
| 2012/0211946 A1 | 8/2012 | Halili et al. |
| 2012/0215183 A1 | 8/2012 | Halili et al. |
| 2012/0220936 A1 | 8/2012 | Miller et al. |
| 2012/0289900 A1 | 11/2012 | Chong et al. |
| 2012/0296307 A1 | 11/2012 | Holt et al. |
| 2013/0006191 A1 | 1/2013 | Jugl et al. |
| 2013/0006213 A1 | 1/2013 | Arnitz et al. |
| 2013/0060232 A1 | 3/2013 | Adlon et al. |
| 2013/0174518 A1 | 7/2013 | Tachikawa et al. |
| 2013/0218092 A1 | 8/2013 | Davies et al. |
| 2013/0218093 A1 | 8/2013 | Markussen et al. |
| 2013/0237916 A1 | 9/2013 | Hanson et al. |

(56) References Cited

U.S. PATENT DOCUMENTS

| | | |
|---|---|---|
| 2013/0253472 A1 | 9/2013 | Cabiri |
| 2013/0267896 A1 | 10/2013 | Dogwiler et al. |
| 2013/0289518 A1 | 10/2013 | Butler et al. |
| 2013/0296779 A1 | 11/2013 | Kuehne et al. |
| 2013/0310800 A1 | 11/2013 | Yodfat et al. |
| 2014/0025008 A1 | 1/2014 | Sims |
| 2014/0074037 A1 | 3/2014 | Bornhoft |
| 2014/0081239 A1 | 3/2014 | Cronenberg |
| 2014/0110370 A1 | 4/2014 | Holt et al. |
| 2014/0121598 A1 | 5/2014 | Katase |
| 2014/0121600 A1 | 5/2014 | McConnell et al. |
| 2014/0121633 A1 | 5/2014 | Causey et al. |
| 2014/0135693 A1 | 5/2014 | Chappel et al. |
| 2014/0135695 A1 | 5/2014 | Grant et al. |
| 2014/0148784 A1 | 5/2014 | Anderson et al. |
| 2014/0207104 A1 | 7/2014 | Vouillamoz et al. |
| 2014/0213975 A1 | 7/2014 | Clemente et al. |
| 2014/0213977 A1 | 7/2014 | Miller et al. |
| 2014/0221930 A1 | 8/2014 | Kuster et al. |
| 2014/0243786 A1 | 8/2014 | Gilbert et al. |
| 2014/0276431 A1 | 9/2014 | Estes et al. |
| 2014/0276563 A1 | 9/2014 | Cole et al. |
| 2014/0276576 A1 | 9/2014 | Cole et al. |
| 2014/0288511 A1 | 9/2014 | Tan-Malecki et al. |
| 2014/0323971 A1 | 10/2014 | Zhou |
| 2014/0323989 A1 | 10/2014 | Baker et al. |
| 2014/0358113 A1 | 12/2014 | Mernoe et al. |
| 2014/0358119 A1 | 12/2014 | Searle et al. |
| 2014/0364808 A1 | 12/2014 | Niklaus et al. |
| 2014/0378891 A1 | 12/2014 | Searle et al. |
| 2014/0378943 A1 | 12/2014 | Geipel |
| 2015/0011976 A1 | 1/2015 | Vouillamoz et al. |
| 2015/0038939 A1 | 2/2015 | Estes et al. |
| 2015/0057613 A1 | 2/2015 | Clemente et al. |
| 2015/0057615 A1 | 2/2015 | Mernoe, V et al. |
| 2015/0065959 A1 | 3/2015 | Carter et al. |
| 2015/0105720 A1 | 4/2015 | Montalvo et al. |
| 2015/0119797 A1 | 4/2015 | Cabiri |
| 2015/0119821 A1 | 4/2015 | Schmitz et al. |
| 2015/0157788 A1 | 6/2015 | Gescheit et al. |
| 2015/0190588 A1 | 7/2015 | Hanson et al. |
| 2015/0224253 A1 | 8/2015 | Cabiri |
| 2015/0246176 A1 | 9/2015 | Navarro et al. |
| 2015/0258273 A1 | 9/2015 | Payne et al. |
| 2015/0374919 A1 | 12/2015 | Gibson |
| 2016/0166765 A1 | 6/2016 | Tan-Malecki et al. |
| 2016/0199578 A1 | 7/2016 | Tan-Malecki et al. |
| 2016/0199582 A1 | 7/2016 | Tan-Malecki et al. |
| 2016/0199583 A1 | 7/2016 | Tan-Malecki et al. |
| 2016/0296704 A1 | 10/2016 | Gibson |
| 2018/0256821 A1 | 9/2018 | Tan-Malecki et al. |

FOREIGN PATENT DOCUMENTS

| | | |
|---|---|---|
| CN | 102149416 A | 8/2011 |
| CN | 102481230 A | 5/2012 |
| CN | 202723859 U | 2/2013 |
| EP | 0602883 A2 | 6/1994 |
| EP | 1927372 A1 | 6/2008 |
| EP | 2248832 A1 | 11/2010 |
| EP | 2554207 A1 | 2/2013 |
| GB | 708707 A | 5/1954 |
| GB | 718837 A | 11/1954 |
| GB | 722166 A | 1/1955 |
| GB | 989185 A | 4/1965 |
| GB | 1159664 A | 7/1969 |
| GB | 2467904 A | 8/2010 |
| JP | 126230 B | 5/1938 |
| JP | S4020079 B | 12/1963 |
| JP | 39-009343 B | 6/1964 |
| JP | S39009343 B | 6/1964 |
| JP | S508273 B1 | 4/1975 |
| JP | S51398 B1 | 1/1976 |
| JP | S645565 A | 1/1989 |
| JP | S6470070 A | 3/1989 |
| JP | H03168154 A | 7/1991 |
| JP | H06209996 A | 8/1994 |
| JP | H07124256 A | 5/1995 |
| JP | H07148258 A | 6/1995 |
| JP | 2001524362 A | 12/2001 |
| JP | 2002-505601 A | 2/2002 |
| JP | 2002507459 A | 3/2002 |
| JP | 2003527159 A | 9/2003 |
| JP | 2004305621 A | 11/2004 |
| JP | 2004-538043 A | 12/2004 |
| JP | 2007117379 A | 5/2007 |
| JP | 2007209675 A | 8/2007 |
| JP | 2009511192 A | 3/2009 |
| JP | 2009207619 A | 9/2009 |
| JP | 2012500679 A | 1/2012 |
| JP | 2012528636 A | 11/2012 |
| JP | 2012528639 A | 11/2012 |
| JP | 2013509925 A | 3/2013 |
| TW | M261223 U | 4/2005 |
| TW | 201100135 A | 1/2011 |
| WO | WO-88/02265 A1 | 4/1988 |
| WO | WO-95/12482 A1 | 5/1995 |
| WO | WO-98/57683 A1 | 12/1998 |
| WO | WO-99/48546 A1 | 9/1999 |
| WO | WO-0130424 A1 | 5/2001 |
| WO | WO-2004/096113 A2 | 11/2004 |
| WO | WO-2007047403 A1 | 4/2007 |
| WO | WO-2007/095297 A2 | 8/2007 |
| WO | WO-2008/083209 A2 | 7/2008 |
| WO | WO-2009/029010 A1 | 3/2009 |
| WO | WO-2010/022870 A1 | 3/2010 |
| WO | WO-2010/029054 A1 | 3/2010 |
| WO | WO-2010098323 A1 | 9/2010 |
| WO | WO-2010/139669 A1 | 12/2010 |
| WO | WO-2010/139672 A1 | 12/2010 |
| WO | WO-2010149975 A1 | 12/2010 |
| WO | WO-2011/054755 A1 | 5/2011 |
| WO | WO-2011/117287 A1 | 9/2011 |
| WO | WO-2011/122395 A1 | 10/2011 |
| WO | WO-2013032779 A2 | 3/2013 |
| WO | WO-2013055873 A1 | 4/2013 |
| WO | WO-2013/089105 A1 | 6/2013 |
| WO | WO-2014/149357 A1 | 9/2014 |

OTHER PUBLICATIONS

Australian Patent Application No. 2012322796, Examination Report No. 2, issued Sep. 13, 2016.

Australian Patent Application No. 2014238267, Examination Report No. 2, dated Jun. 14, 2019.

Australian Patent Application No. 2014340171, Examination Report No. 1, issued Jun. 12, 2018.

Australian Patent Application No. 2017203992, Examination Report No. 1, issued Nov. 6, 2018.

Chinese Patent Application No. 201480017559.3, First Office Action (English translation), dated Oct. 12, 2018.

Chinese Patent Application No. 201480017559.3, Search Report, dated Sep. 27, 2018.

Chinese Patent Application No. 201480017559.3, Second Office Action, dated Jun. 5, 2019.

Chinese Patent Application No. 201480017559.3, Supplemental Search Report, dated May 28, 2019.

Chinese Patent Application No. 201480058204.9, First Office Action, dated Nov. 28, 2018.

Chinese Patent Application No. 201480058204.9, Search Report, dated May 28, 2019.

Chinese Patent Application No. 201480058204.9, Search Report, dated Nov. 19, 2018.

Chinese Patent Application No. 201480058204.9, Second Office Action, dated Jun. 4, 2019.

Communication pursuant to Article 94(3) EPC dated Mar. 6, 2018 and issued in European Patent Application No. 14792707.3.

Communication pursuant to Article 94(3) EPC issued in European Patent Application No. EP1615530.5, dated Aug. 14, 2017.

Communication pursuant to Article 94(3) EPC issued in European Patent Application No. EP16156583.3, dated Aug. 22, 2017.

(56) References Cited

OTHER PUBLICATIONS

Communication under Rule 71(3) EPC issued in EPO Patent Application No. 16155526.3, dated Nov. 5, 2018.
Eurasian patent application No. 201490755, Official Action (translation) (Jun. 27, 2017).
Eurasian patent application No. 201490755, Official Action (translation) (Oct. 31, 2016).
European Office Action for Application No. 12 784 119.5 dated Dec. 4, 2015.
European Patent Application No. 14708447.9, Communication pursuant to Article 94(3) EPC, dated Jan. 12, 2018.
European Patent Application No. 16155526.3, Communication pursuant to Article 94(3) EPC, dated Jan. 26, 2018.
European Patent Application No. 16155530.5, Communication Pursuant to Article 94(3) EPC, dated Jul. 12, 2019.
European Patent Application No. 16155530.5, Communication pursuant to Article 94(3) EPC, dated Sep. 3, 2018.
European Patent Application No. 16156583.3, Communication Pursuant to Article 94(3) EPC, dated Jul. 6, 2020.
European Patent Application No. 16156583.3, Communication pursuant to Article 94(3) EPC, Sep. 3, 2018.
European Patent Application No. 16156583.3, Communication Pursuant to Article 94(3), dated Jul. 19, 2019.
European Patent Application No. 16156583.3, Result of Consultation, Jul. 10, 2019.
European Patent Application No. 17187106.4, Communication Pursuant to Article 94(3) EPC, dated Dec. 11, 2018.
European Patent Application No. 17187106.4, Extended European Search Report, dated Nov. 30, 2017.
European Patent Application No. 18155148.2, Communication Pursuant to Article 94(3) EPC, dated May 21, 2019.
European Patent Application No. 18186736.7, Communication Pursuant to Article 94(3) EPC, dated Sep. 9, 2019.
European Patent Application No. 18186736.7, Extended European Search Report, dated Nov. 20, 2018.
European Search Report issued in European Patent Application No. 18155148.2, dated May 4, 2018.
Examiner's Decision of Rejection issued in Japanese Patent Application No. 2016-504292, dated May 8, 2018.
Extended European Search Report, European patent application No. 16155526.3, dated Jun. 20, 2016.
Extended European Search Report, European patent application No. EP1615530, dated Jun. 20, 2016.
Extended European Search Report, European patent application No. EP16156580.9, dated Jun. 20, 2016.
Extended European Search Report, European patent application No. EP16156583.3, dated Jun. 20, 2016.
International Preliminary Report on Patentability, corresponding international application No. PCT/US2012/059680, Apr. 15, 2014.
International Preliminary Report on Patentability, International Application No. PCT/US2014/017641, dated Sep. 22, 2015.
International Preliminary Report on Patentability, International Application No. PCT/US2014/061675, dated Apr. 26, 2016.
International Search Report and Written Opinion, corresponding international application No. PCT/US2012/059680, mailing date Jan. 30, 2013.
International Search Report and Written Opinion, International Application No. PCT/US2014/061675, mailed Jan. 19, 2015.
International Search Report for Application No. PCT/US2014/017641, dated Jul. 21, 2014.
Israel Patent Application No. 231679, Office Action, dated Apr. 20, 2017.
Israel Patent Application No. 260100, Office Action, dated Oct. 18, 2018.
Israeli Patent Application No. 243979, Office Action, dated Jun. 23, 2019.
Japanese Patent Application No. 2016-504292, Appeal No. 2018-11867 (against the Examiner's Decision of Rejection), mailed Sep. 10, 2019.
Japanese Patent Application No. 2016-504292, Re-examination Report, dated Nov. 20, 2018.
Japanese Patent Application No. 2016-550467, Notice of Rejection, dated Apr. 16, 2019.
Japanese Patent Application No. 2018-165651, Notice of Rejection, mailed Jul. 23, 2019.
Japanese Patent Application No. 2018-178432, Notice of Rejection, mailed Sep. 10, 2019.
Japanese Patent Application No. 2020-190671, Office Action, mailed Oct. 5, 2021.
Korean Patent Application No. 10-2014-7012457, Notice of Preliminary Rejection, dated Apr. 17, 2019.
Korean Patent Application No. 10-2015-7030084, Notice of Preliminary Rejection, dated Nov. 18, 2020.
Mexican Application No. Application No. MX/a/2016/005312, Office Action, issued Aug. 20, 2019.
Mexican Patent Application No. MX/a/2014/004505, Official Action, dated Mar. 28, 2017.
Mexican Patent Application No. MX/a/2014/004505, Official Action, dated Oct. 4, 2017.
Mexican Patent Application No. MX/a/2015/013533, Office Action, dated Jul. 1, 2019.
Mexican Patent Application No. MX/a/2015/013533, Office Action, dated Nov. 27, 2018.
Notice of Rejection (translation), Japanese patent application No. 2014-535858, mailed Aug. 2, 2016.
Notice of Rejection mailed on Jan. 23, 2018 in counterpart Japanese Patent Application No. 2014-535858, and translation thereof.
Notice of Rejection mailed on Jun. 20, 2017 in Japanese Application No. 2014-535858 and translation thereof.
Notice of Rejection mailed on Oct. 17, 2017 in Japanese Patent Application No. 2016-504292 and translation thereof.
Office Action issued in Australia Patent Application No. 2014238267, dated Aug. 9, 2018.
Office Action issued in Canada Patent Application No. 2,851,521, dated Aug. 24, 2018.
Office Action issued in Israel Patent Application No. 239799, dated Oct. 7, 2018. .
Office Action issued in Japan Patent Application No. 2016-550467, dated Aug. 14, 2018.
Office Action issued in Mexican Patent Application No. MX/a/2015/013533, dated Aug. 22, 2018.
Office Action issued in U.S. Appl. No. 14/763,429, dated Aug. 16, 2018.
Office Action issued in U.S. Appl. No. 14/763,429, dated Feb. 13, 2018. .
Office Action issued in U.S. Appl. No. 14/916,208, dated Aug. 11, 2018.
Office Action issued in U.S. Appl. No. 14/916,208, dated Jun. 7, 2018.
Office Action issued in U.S. Appl. No. 15/040,308, dated Apr. 2, 2018.
Office action issued in U.S. Appl. No. 15/040,308, dated Aug. 6, 2018.
Office Action issued in U.S. Appl. No. 15/040,335, dated Jun. 21, 2018.
Office Action issued in U.S. Appl. No. 15/040,335, dated Oct. 24, 2018.
Office Action issued in U.S. Appl. No. 15/047,792, dated Apr. 2, 2018.
Office Action issued in U.S. Appl. No. 15/047,792, dated Aug. 2, 2018.
Office Action issued in U.S. Appl. No. 15/047,815, dated May 24, 2018.
Office Action issued on Mar. 15, 2017 in Taiwanese Application No. 103108887 and translation thereof.
Official Action (translation), Eurasian patent application No. 201490755 (Feb. 29, 2016).
Patent Examination Report No. 1, Australian Patent Application No. 2012322796, issued May 31, 2016.
Search Report and Written Opinion for Singapore Patent Application No. 11201507878S dated Nov. 28, 2016.

(56) References Cited

OTHER PUBLICATIONS

Search Report issued in counterpart Taiwanese Patent Application No. 106134719 on Jul. 4, 2018.
Singapore Patent Application No. 11201507878S, Written Opinion, dated Feb. 4, 2019.
Singapore Patent Application No. 11201602876W, Written Opinion, dated Jul. 11, 2017.
Text of First Office Action (translation), Chinese patent application No. 201280050454.9, dated Jul. 15, 2015).
Text of Second Office Action (translation), Chinese patent application No. 201280050454.9, dated Mar. 18, 2016.
U.S. Appl. No. 14/763,429, Final Office Action, dated May 4, 2020.
U.S. Appl. No. 14/916,208, Final Office Action, Jan. 28, 2021.
U.S. Appl. No. 14/916,208, Nonfinal Office Action, dated Jan. 13, 2020.
U.S. Appl. No. 14/916,208, Nonfinal Office Action, dated Sep. 22, 2020.
U.S. Appl. No. 14/916,208, Notice of Allowance, dated Apr. 28, 2021.
U.S. Appl. No. 15/040,308, Nonfinal Office Action, dated Feb. 26, 2019.
U.S. Appl. No. 15/040,335, Notice of Allowance, dated Feb. 7, 2019.
U.S. Appl. No. 15/047,792, Nonfinal Office Action, dated Feb. 15, 2019.
U.S. Appl. No. 15/047,815, Decision on Appeal, dated Nov. 27, 2020.
U.S. Appl. No. 15/047,815, Decision on Request for Rehearing, dated Mar. 19, 2021.
U.S. Appl. No. 15/047,815, Notice of Allowance, dated May 27, 2021.
U.S. Appl. No. 16/401,471, Nonfinal Office Action, dated Dec. 16, 2020.
U.S. Appl. No. 16/687,254, Final Office Action, dated Dec. 22, 2020.
U.S. Appl. No. 16/687,254, Nonfinal Office Action, dated Jul. 27, 2020.
U.S. Appl. No. 16/687,254, Notice of Allowance dated Mar. 10, 2021.
U.S. Appl. No. 16/839,267, Final Office Action, dated Mar. 23, 2021.
U.S. Appl. No. 16/839,267, Nonfinal Office Action, dated Dec. 15, 2020.
U.S. Appl. No. 14/350,687, Office Action, dated Aug. 3, 2016.
U.S. Appl. No. 14/350,687, Office Action, dated Feb. 19, 2016.
U.S. Appl. No. 14/350,687, Office Action, dated Mar. 31, 2017.
U.S. Appl. No. 14/763,429, Final Office Action, dated Aug. 6, 2019.
U.S. Appl. No. 14/763,429, Nonfinal Office Action, dated Jan. 25, 2019.
U.S. Appl. No. 14/916,208, Final Office Action, dated Nov. 8, 2018.
U.S. Appl. No. 15/047,815, Final Office Action, dated Nov. 16, 2018.
U.S. Appl. No. 15/047,815, Final Office Action, dated Oct. 4, 2019.
U.S. Appl. No. 15/047,815, Nonfinal Office Action, dated May 2, 2019.
U.S. Appl. No. 15/974,354, Nonfinal Office Action, dated Oct. 24, 2019.
Written Opinion dated Jan. 18, 2018 and issued in counterpart Singaporean Patent Application No. 11201507878S.
Written Opinion for Application No. PCT/US2014/017641, dated Sep. 22, 2015.
Written Opinion for Singapore Application No. 11201602876W, dated Jan. 3, 2017.

\* cited by examiner

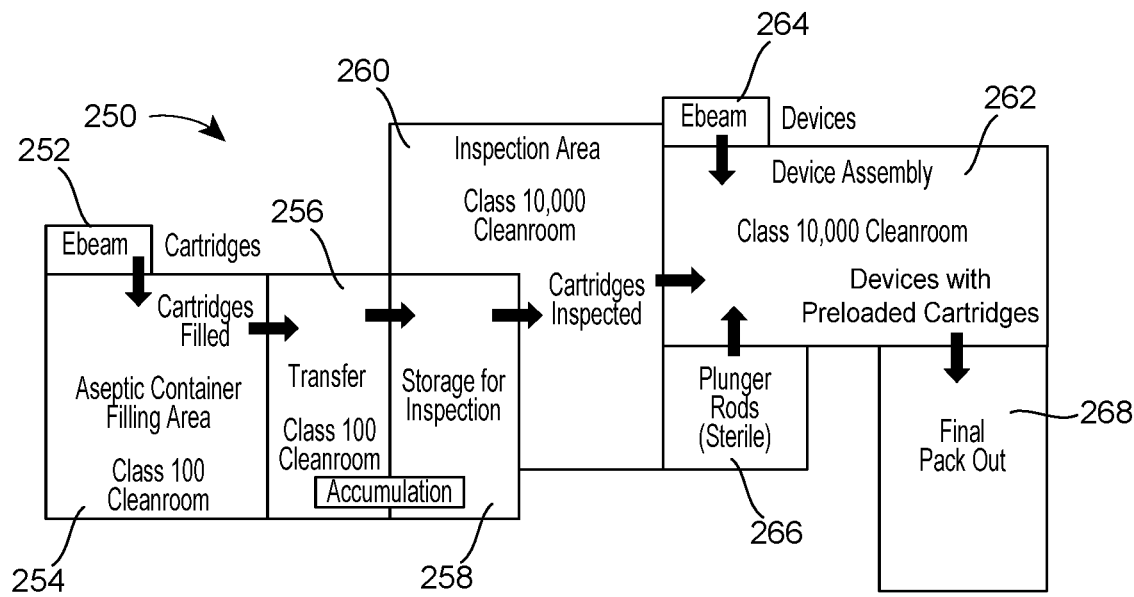
*FIG. 4*
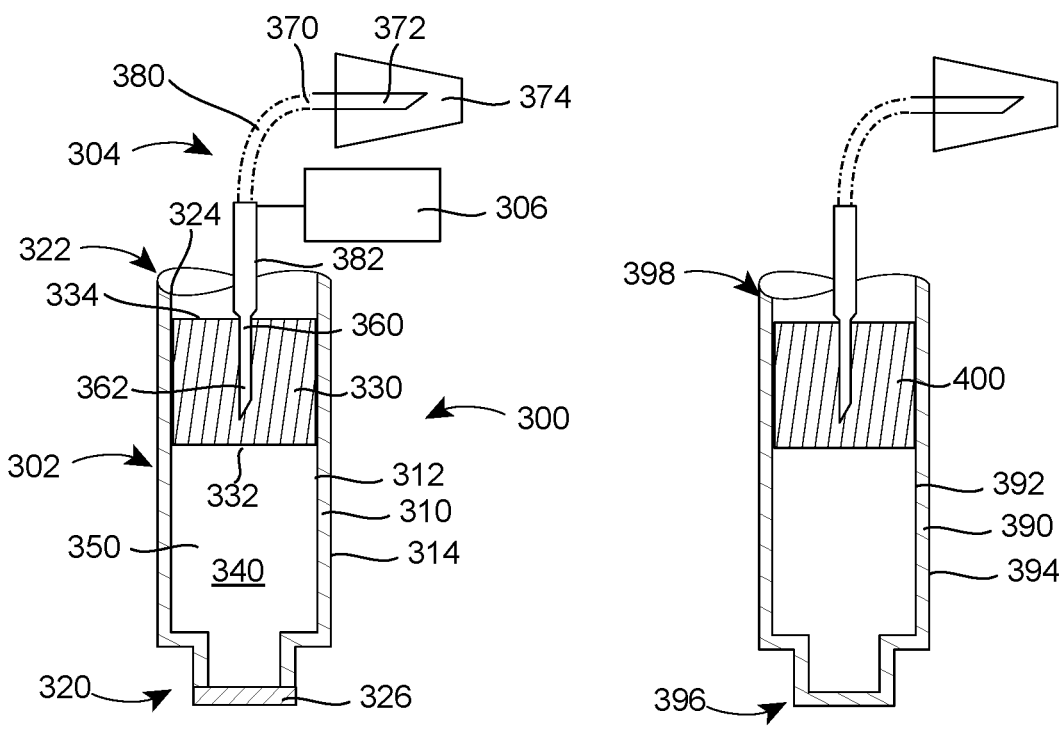
*FIG. 5*       *FIG. 6*

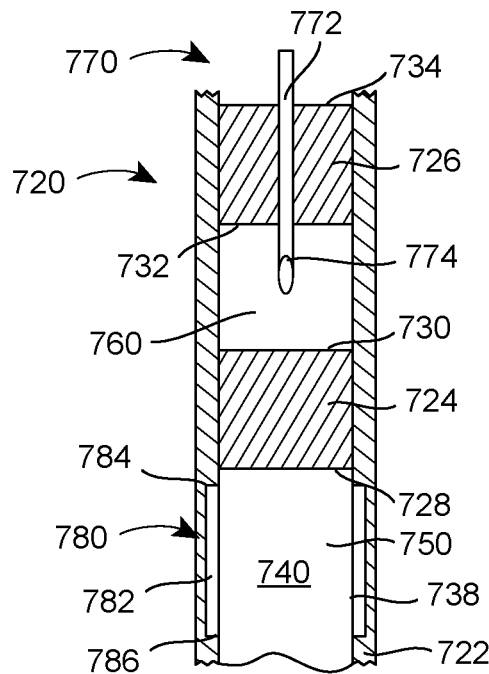
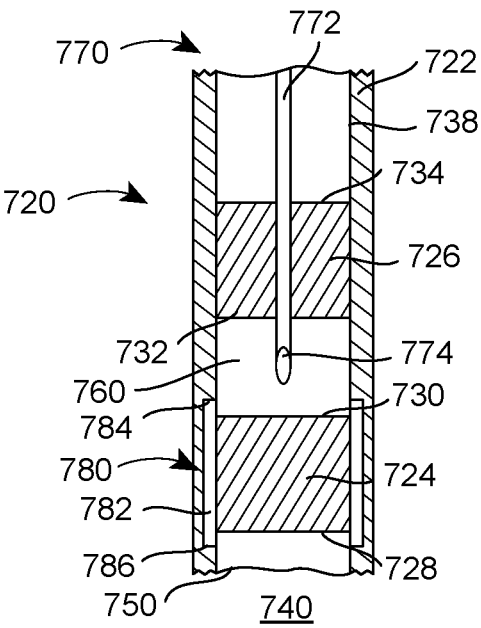
*FIG. 10*   *FIG. 11*
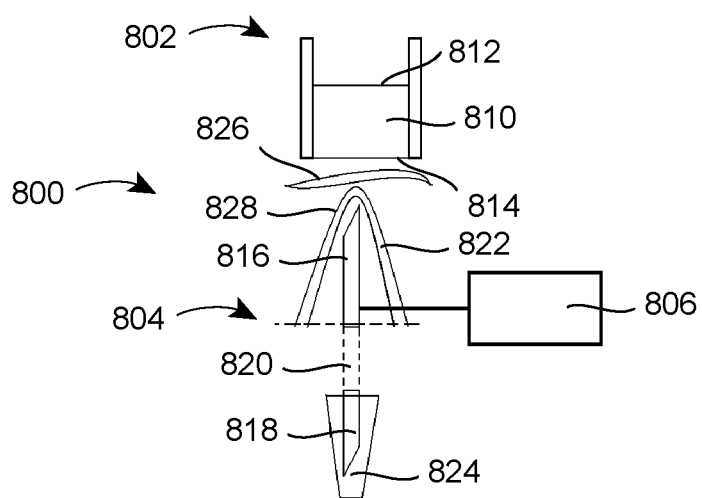
*FIG. 12*

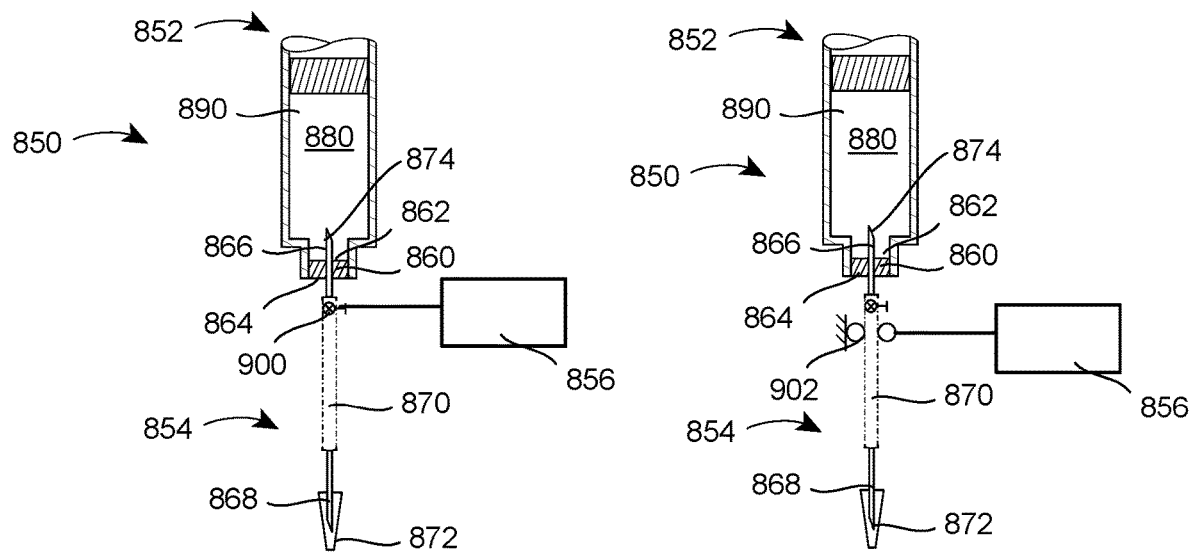
*FIG. 13*     *FIG. 14*
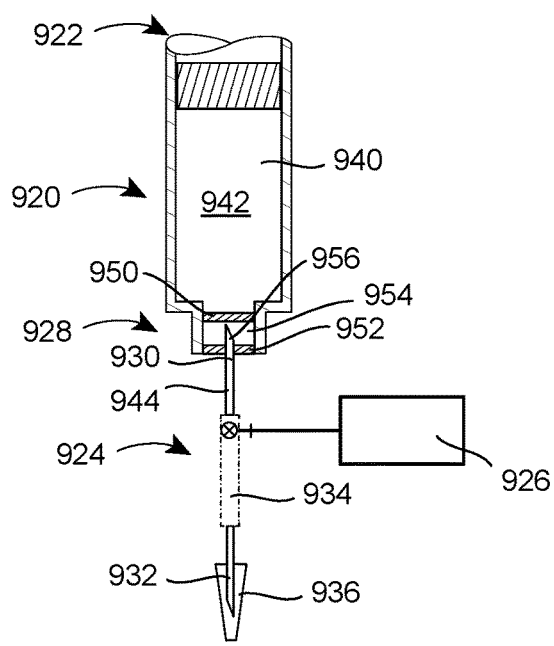
*FIG. 15*

INJECTOR AND METHOD OF ASSEMBLY

CROSS-REFERENCE TO RELATED APPLICATIONS

This is a continuation of U.S. patent application Ser. No. 17/350,883, filed Jun. 17, 2021, which is a continuation of U.S. patent application Ser. No. 16/687,254, filed Nov. 18, 2019, which is a continuation of U.S. patent application Ser. No. 15/040,308, filed Feb. 10, 2016, which is a continuation of U.S. patent application Ser. No. 14/350,687, filed Apr. 9, 2014, which is the U.S. National Stage of PCT/US12/59680, filed Oct. 11, 2012, which claims the benefit of priority of U.S. Provisional Application No. 61/547,667, filed Oct. 14, 2011. The entirety of the foregoing is expressly incorporated herein by reference.

BACKGROUND

This patent is directed to an injector and a method of assembling the injector, and, in particular, to a prefilled injector and a method of assembling the prefilled injector.

Injectors are used to deliver medical fluids, such as liquid drugs, to a patient. In particular, the injector will provide the fluid to the patient through a needle, cannula or catheter that defines a flow path into the patient. Certain injectors have a reservoir that is assembled by the manufacturer already connected to the flow path. However, these reservoirs are typically provided empty by the manufacturer to the patient or healthcare provider (e.g., doctor, nurse, healthcare assistant, etc.), and then the reservoir is filled at the time of use. Alternatively, the injector may be used in combination with a reservoir that is provided to the patient or healthcare provider prefilled.

In either case, the injector must be prepared prior to use. For example, if the reservoir is provided empty, then the reservoir must be filled. To do this, a syringe is filled with the drug to be delivered, and then the drug is injected into the reservoir through an inlet port. Prior to the injection, the inlet port must be sterilized by swabbing the outer surface with an alcohol wipe, for example. Similarly, before the prefilled reservoir is connected to the flow path in the alternative injector, the mating connectors must be sterilized, by swabbing the surface with an alcohol wipe.

In either event, the use of the injector requires additional material and time.

As set forth in more detail below, the present disclosure sets forth an improved injector embodying advantageous alternatives to the conventional devices and methods discussed above.

SUMMARY

According to an aspect of the present disclosure, an injector may include a container having a wall with an interior surface and a seal assembly with an interior surface, the interior surfaces of the wall and the seal assembly defining a closed sterile reservoir filled with a drug product. The injector may also include a fluid delivery system comprising a clean, unsheathed, rigid container needle having a point disposed only partially through the seal assembly in a storage state, and disposed through the interior surface of the seal assembly into the sterile reservoir in a delivery state. Further, the injection may include an actuator that is adapted to move the container needle from the storage state to the delivery state.

The wall of the container may be a rigid wall or a flexible wall.

According to any of the foregoing, the seal assembly may be a flexible unitary wall having an interior surface that defines the interior surface of the seal assembly. The flexible unitary wall may define a septum disposed across the opening and fixedly attached to the wall of the container. Alternatively, the wall of the container may define a bore, and the unitary flexible wall may define a stopper that is moveable along the bore. In such a case, the wall of the container may define a closed end opposite the stopper and an open end in which the stopper is disposed. As a further alternative, the wall of the container may define a bore with an opening in fluid communication with a first end of the bore, and the unitary flexible wall defines a septum disposed across the opening and fixedly attached to the wall of the container, the container further comprising a stopper that is disposed within a second end of the bore and is moveable along the bore.

In the alternative to the preceding paragraph, the seal assembly may include a flexible wall with an interior surface that defines the interior surface of the seal assembly, and a clean barrier disposed exterior of the flexible wall to define an enclosed clean space between the flexible wall and the clean barrier, the point of the container needle disposed through the clean barrier into the clean space in the storage state. The wall of the container may define a bore, and the flexible wall and the clean barrier may each define a stopper that is moveable along the bore. In addition, the container may include a vent in fluid communication with the space between the clean barrier and the flexible wall, which vent may be formed in the clean barrier or within the interior surface of the wall of the container. Further, the wall of the container may define a closed end opposite the stoppers and an open end in which the stoppers are disposed. In the alternative, the wall of the container may define a bore with an opening in fluid communication with a first end of the bore, and the flexible wall and the clean barrier each may define a septum disposed across the opening, the container further including a stopper that is disposed within a second end of the bore and is moveable along the bore.

According to any of the foregoing, the fluid delivery system may include clean flexible tubing connected at a first end to the rigid container needle and a second end to a clean rigid injection needle received within a clean cover that closes off the clean rigid injection needle.

According to any of the foregoing, the actuator may be adapted to move the container needle repeatedly between the storage state and the delivery state.

According to any of the foregoing, the actuator may be adapted to delay movement of the container needle from the storage state to the delivery state after an input is received.

According to any of the foregoing, the injector may include a mechanical, electro-mechanical, or electrical input device coupled to the actuator.

According to any of the foregoing, the drug product may include a volume of an erythropoiesis stimulating agent, a granulocyte colony-stimulating factor, a TNF blocker, a pegylated granulocyte colony-stimulating factor, inter-leukin-receptor specific antibody, IGF-receptor (Insulin Growth Factor receptor) specific antibody, TGF-specific antibody, or PCSK9 (Proprotein Convertase Subtilisin/Kexin Type 9)—specific antibody.

According to another aspect of the present disclosure, a method of assembling an injector may include filling a sterile reservoir of a container with a drug product under sterile conditions, the reservoir defined by an interior surface of a wall of the container and an interior surface of a seal assembly. The method may also include inserting a point of a clean, unsheathed, rigid container needle partially through the seal assembly under clean room conditions subsequent to filing the sterile reservoir to define a storage state, and attaching the container needle to an actuator under clean room conditions, the actuator adapted to move the container needle from the storage state to a delivery state wherein the container needle is disposed through the interior surface of the seal assembly into the sterile reservoir.

According to this aspect, the wall of the container may be a rigid wall or a flexible wall.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4 is a schematic of a manufacturing facility wherein injectors according to the present disclosure may be filled and assembled;

FIG. 5 is a cross-sectional view of an alternative embodiment of an injector according to the present disclosure, with a unsheathed, rigid container needle in a storage state wherein the needle partially penetrates a unitary wall of the container;

FIG. 6 is a cross-sectional view of a further alternative embodiment of an injector according to the present disclosure, with a unsheathed, rigid container needle in a storage state wherein the needle partially penetrates a unitary wall of the container;

FIG. 10 is a cross-sectional view of an additional variant to the embodiment of FIG. 8 including bypasses to evacuate a clean space between a flexible wall and an exteriorly disposed clean barrier as an associated container needle is moved between a storage state and a delivery state;

FIG. 11 is a cross-sectional view of the container of FIG. 10 in an intermediate state with the bypasses in fluid communication with a clean space defined between a flexible wall and a clean barrier;

FIG. 12 is a schematic view of further assembly of container and fluid delivery system that may be used to preserve a sterile condition within the container;

FIG. 13 is a cross-sectional view of an injector according to a still further embodiment of the present disclosure where a sterile condition is maintained in a reservoir until actuation of the fluid delivery system;

FIG. 14 is a cross-sectional view of a variant of the injector illustrated in FIG. 13;

FIG. 15 is a cross-sectional view of a further variant of the injector illustrated in FIG. 13.

DETAILED DESCRIPTION OF VARIOUS EMBODIMENTS

Figure 1:
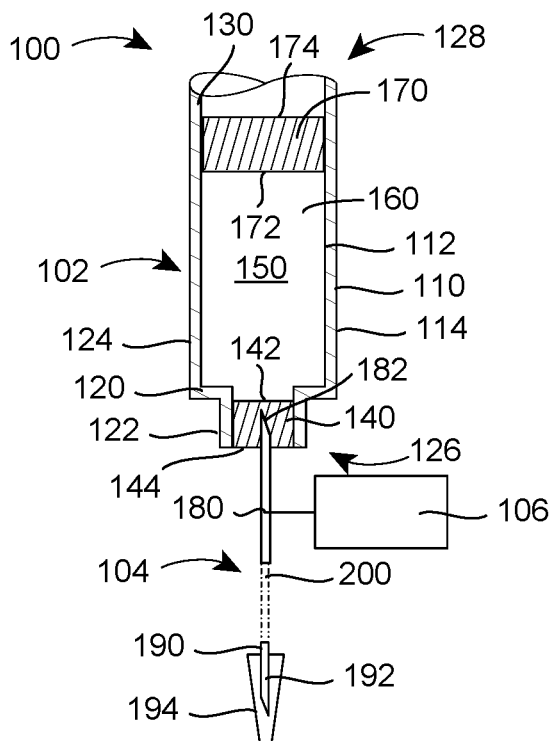
FIG. 1 is a cross-sectional view of an embodiment of an injector according to the present disclosure, with a unsheathed, rigid container needle in a storage state wherein the needle partially penetrates a unitary wall of the container.

Although the following text sets forth a detailed description of different embodiments of the invention, it should be understood that the legal scope of the invention is defined by the words of the claims set forth at the end of this patent. It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, which would still fall within the scope of the claims defining the invention. Along these lines then, several embodiments according to the present disclosure are illustrated in FIGS. 1-3 and 5-15.

In general terms, an injector according to the present disclosure includes a container, a fluid delivery system and an actuator. While reference is made to an injector, which in some instances may refer to a delivery device that ensures that a set volume of drug product is delivered, it will be understood that this disclosure also encompasses infusion devices, which in some instances may refer to a delivery device that ensures that a particular rate of delivery is achieved. It should also be understood that the terms injector and infuser may be used interchangeably when referring to embodiments in the specification.

As illustrated in FIGS. 1-3 and 5-11, the container may include a wall with an interior surface and a seal assembly with an interior surface, the interior surfaces of the wall and the seal assembly defining a closed sterile reservoir filled with a drug product. Moreover, the fluid delivery system illustrated in these embodiments may include a clean, unsheathed, rigid container needle having a point disposed only partially through the seal assembly in a storage state, and disposed through the interior surface of the seal assembly into the sterile reservoir in a delivery state. The injector may also include an actuator that is adapted to move the container needle from the storage state to the delivery state, which may involve movement of the needle relative to the container or of the container relative to the needle, as is discussed in greater detail below.

As is illustrated in FIGS. 1, 3, and 4-6, the seal assembly may be a flexible unitary wall having an interior surface that defines the interior surface of the seal assembly, and the point of the container needle may be disposed partially into the unitary wall. Alternatively, as illustrated in FIGS. 7-11, the seal assembly may include a flexible wall with an interior surface that defines the interior surface of the seal assembly, and a clean barrier disposed exterior of the flexible wall to define an enclosed clean space between the flexible wall and the clean barrier. According to such embodiments, the point of the container needle is disposed through the clean barrier into the clean space in the storage state.

Still further alternatives will be discussed in the context of each of the embodiments illustrated herein.

Referring then to FIG. 1, an injector 100 is illustrated therein. The injector 100 includes a container 102, a fluid delivery system 104, and an actuator 106.

The container 102 (which also may be referred to as a cartridge herein) includes a wall 110 with an interior surface 112 and an exterior surface 114. While a unitary (i.e., one-piece) wall 110 has been illustrated in FIG. 1 that defines both the interior and exterior surfaces 112, 114, it will be understood that according to other embodiments the wall 110 may include a plurality of layers with different layers defining the interior and exterior surfaces 112, 114.

According to certain embodiments of the present disclosure, the wall 110 is rigid. According to other embodiments, the wall 110 may be flexible, whether according to the nature of the material that defines the wall or according to the nature of the structure of wall (e.g., a bellows construction). The wall 110 may be made of glass, metal, or polymer, for example. In particular, polymer versions may be made of polycarbonate, polypropylene, polyethylene (such as high density polyethylene), polytetrafluoroethylene, cyclic olefin polymer, cyclic olefin copolymer, Crystal Zenith olefinic polymer (available from Daikyo Seiko, Ltd., Japan), nylon, or engineering resins, for example. As to flexible versions of the wall 110, butyl rubber, silicon-based rubber, latex-based rubber, coated rubber, as well as multi-layer polymer films, such as may include polyethylene (such as low density polyethylene) and polypropylene, may be used.

The wall 110 may have a generally cylindrical shape, which a shoulder 120 separating a first cylindrical section 122 having a first cross-sectional diameter from a second cylindrical section 124 having a second cross-sectional diameter, the first cross-sectional diameter being smaller than the second cross-sectional diameter. The wall 110 may also define two opposed, open ends 126, 128. The wall 110, or more particularly the interior surface 112 of the wall 110, may also define a bore 130.

The container 102 may include a flexible unitary wall 140 (which may also be referred to as a seal or septum) having an interior surface 142 and an exterior surface 144. The wall 140 may be disposed in the first open end 126 defined by the wall 110 and fixedly attached to the wall 110 of the container 102 such that there is limited relative movement between the wall 140 and the wall 110, for example at the points of attachment of the wall 140 to the wall 110 across the open end or opening 126. Moreover, the interior surfaces 112, 142 of the wall 110 and the flexible wall 140 may define, at least in part, a closed sterile reservoir 150 that is filled with a drug product 160, described in greater detail below. The wall 140 may be made of bromobutyl, chlorobutyl, or chlorobromobutyl rubber, fluoropolymer rubber, natural rubber, silicon-based rubber, silicon, or santoprene, for example.

The container 102 may also include a stopper or piston 170 with interior and exterior surfaces 172, 174. The piston 170 may be received within the end 128 defined by the wall 110, and may be moveable along the bore 130 between the ends 126, 128 of the container 102. According to such an embodiment, the reservoir 150 within which the drug product 160 is disposed may be defined by the interior surfaces 112, 142, 172 of the walls 110, 140 and piston 170.

Figure 2:
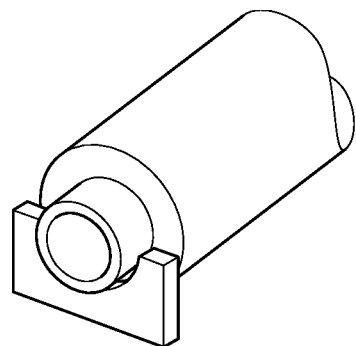
FIG. 2 is a perspective view of a jig used with the container of the injector of FIG. 1 to control the penetration of the flexible unitary wall of the container by the container needle.

The container 102 may be used in conjunction with the fluid delivery system 104, the relevant portions of which are illustrated in FIG. 1. In particular, the fluid delivery system 104 may include a clean, unsheathed, rigid container needle 180 having a point 182. As illustrated, the point 182 is disposed only partially into the flexible wall 140 in a storage state. The penetration of the point 182 of the needle 180 into the wall 140 may be controlled through a number of methods and/or mechanisms. For example, FIG. 2 illustrates a jig that may be used in combination with the container 102 to control the depth to which the point 182 penetrates the wall 140.

The fluid delivery system 104 may also include an injection needle 190 with a point 192. The point 192 of the injection needle 190 may be covered with a needle shield 194 to prevent contact with and contamination of the point 192. The container needle 180 and the injection needle 190 may be connected by a cannula or tube 200, which may be a flexible cannula according to certain embodiments of the present disclosure. The needle 190, like the needle 180, may be made of stainless steel, for example.

Fluid delivery system 104 may be used in conjunction with the actuator 106, mentioned previously and illustrated schematically in FIG. 1. The actuator 106 may be adapted to move the container needle 180 between the storage state illustrated in FIG. 1 and a delivery state illustrated in FIG. 3. In the delivery state, the container needle 180 is disposed through the interior surface 142 of the flexible wall 140 into the sterile reservoir 150.

The movement of the needle 180 between the states may occur in a variety of fashions. For example, the needle 180 may be held fixed relative to the housing of the injector 100, and the container 102 may move relative to the needle 180 and the housing. Alternatively, the container 102 may be held fixed relative to the housing, and the needle 180 may be moved relative to the container 102 and the housing. It may also be possible for both container 102 and needle 180 to move relative to the housing of the injector 100. It will be understood that all of these actions may be embraced within the statement that the actuator 106 is adapted to move the container needle 180 between the storage and delivery states.

The actuator 106 may be mechanical, electro-mechanical, or electrical. For example, the actuator 106 may include a solenoid, motor-driven lever, motor with associated gearing, etc. It may even be possible to provide a tab or button attached to the container 102 or the needle 180 to permit the user to achieve the relative motion between the container 102 and the needle 180 manually. In fact, the container 102 may be received within a tab or button that is depressed into the housing when the injector 100 is activated to move the container 102 relative to the (fixed) needle 180.

The actuator 106 may move the container needle 180 between storage and delivery states by moving the needle 180 from the storage state to the delivery state, or by moving the needle 180 from the delivery state to the storage state. In fact, the actuator may move the container needle 180 between the storage and delivery states repeatedly (i.e., multiple times or repetitions). Furthermore, the actuator 106 may move the container needle 180 immediately upon receipt of an input or signal (e.g., as generated through the depression or manipulation of a button, switch or other input device, which may be mechanical, electro-mechanical or electrical in nature, coupled to the actuator 106), or may delay movement of the container needle 180 between storage and delivery states some period of time after an input is received. According to a particular embodiment, the actuator 106 may delay movement of the needle 180 from the storage state to the delivery state until after such a time delay.

As mentioned previously, the reservoir 150 is described as sterile, while the container needle 180 is described as clean. These terms describe the condition of the reservoir 150 or the needle 180 as a consequence of their assembly under conditions that will ensure a specified level of freedom from contamination, wherein a sterile object or device is understood to have a relatively higher level of freedom from contamination than a clean object or device. By way of non-limiting example, the concepts of sterility and cleanliness may be discussed with reference to the schematic of FIG. 4, which discussion will be recognized applies not only to the embodiment illustrated in FIGS. 1 and 3, but all of the embodiments described herein.

FIG. 4 illustrates a manufacturing facility 250, and may be used to discuss a manufacturing process that is conducted within the facility 250. It will be noted that the facility 250 is divided into a plurality of spaces 252, 254, 256, 258, 260, 262, 264, 266, 268, which divisions may be maintained through the use of permanent or semi-permanent walls or other barriers. As will be understood, certain spaces or regions may be divided without barriers or walls, but may simply be separated on an organizational level instead. Additionally, it will be recognized that a greater or lesser number of spaces or an alternative arrangement of the spaces may be used, such differing numbers or arrangements of spaces being readily determinable by one of ordinary skill in the art.

The components of the container 102 (walls 110, 140, and stopper/piston 170) would enter the facility 250 through space 252, wherein the components are sterilized using e-beam technology, for example. Alternatively, the container components may be sterilized through other currently-known (e.g., treatment with chlorine dioxide or vapor phase hydrogen peroxide) or later-developed sterilization procedures as the components enter the facility 250 at entry points 252, 264, 266. The container 102 would then pass into space 254 for filing with the drug product. The space 254 may be operated as an aseptic Class 100 clean room. A Class 100 clean room is one in which the number of particles of size 0.5 µm or larger permitted per cubic foot of air is less than 100. Once the fill has been performed and the stopper 170 has been disposed in the end 128 of the container 102, the container 102 and drug product 160 is moved through transfer space 256 (also operated as a Class 100 clean room, wherein certain embodiments are also aseptic) before being received within storage space 258.

The containers 102 move from the storage space 258 into inspection area 260 (aseptic in certain embodiments), wherein the containers 102 are inspected prior to assembly with the fluid delivery system 104, actuator 106 and other elements of the injector 100. Because the drug product 160 is contained within the sealed container 102 at this point, the inspection area may be operated as a Class 10,000 clean room. Once inspected, the prefilled, sterile container 102 may be passed from inspection space 260 to assembly space 262.

Similar to the inspection space 260, the assembly space 262 may be operated as an aseptic Class 10,000 clean room. Materials being passed into the clean room from spaces 264, 266 may be in a sterile condition, or may be sterilized using e-beam technology, for example. Within the assembly space 262, the fluid delivery system 104 is connected to the container 102 once the surface 144 of the wall/septum 140 has been sterilized by swabbing the surface 144 with an alcohol wipe, for example. Because of the lower level of cleanliness, the fluid delivery system 104 may be referred to as clean, but not necessarily as sterile. However, because the container needle 180 does not penetrate through the wall 140, the reservoir 150 and the drug product 160 remains sterile (i.e., at the higher level of cleanliness). The remainder of the injector 100 may also be assembled in this space 262 prior to the injector 100 passing into the packaging space 268, with certain aspects of the injector (e.g., the actuator 106) potentially being assembled with the container 102 or the fluid delivery system 104 prior to the assembly of the container 102 and the fluid delivery system 104.

Figure 3:
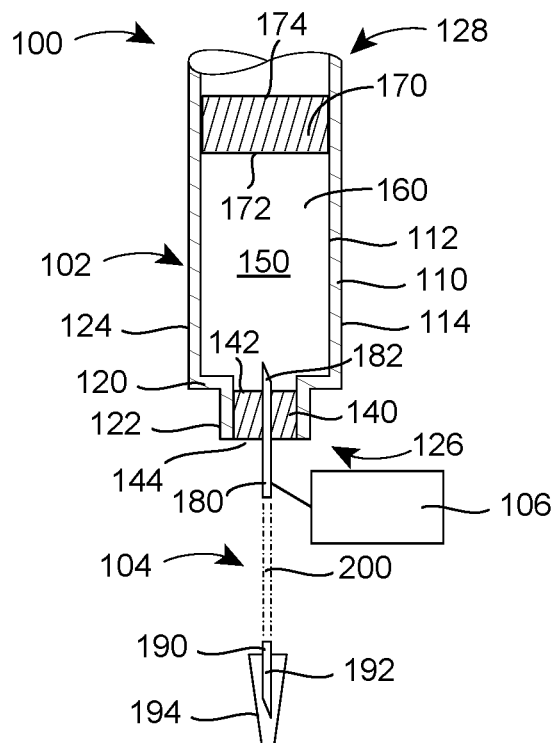
FIG. 3 is a cross-sectional view of the injector of FIG. 1, with the container needle in a delivery state wherein the needle penetrates the unitary wall of the container such that it is disposed through an interior surface of the flexible wall into a sterile reservoir.

It will be recognized that the embodiment of the injector 100 illustrated in FIGS. 1 and 3 is simply an exemplary embodiment according to the present disclosure. To this end, FIGS. 5 and 6 illustrate variants of the injector illustrated in FIGS. 1 and 3.

According to the embodiment of FIG. 5, the injector 300 includes a container 302, a fluid delivery device 304 and an actuator 306. Similar to the embodiment of FIGS. 1 and 3, the container 302 includes a wall 310 with interior and exterior surfaces 312, 314. Moreover, the wall 310 may have two opposed ends 320, 322 with the interior surface 312 of the wall 310 defining a bore 324 between the opposing ends 320, 322.

However, unlike the container 102, the container 302 has a fixed plug 326 that closes the end 320. In addition, while the container 302 has a flexible unitary wall 330 with interior and exterior surfaces 332, 334, the wall 330 is disposed within the end 322 of the container 302, and thus performs the role of the stopper/piston 170 in the container 102. Consequently, the wall 330 is moveable along the bore 324 between the opposing ends 320, 322. Moreover the interior surfaces 312, 332 of the walls 310, 330 define a sterile reservoir 340 in which a drug product 350 is disposed.

According to this embodiment, the fluid delivery device 304 may include a clean, unsheathed, rigid container needle 360 having a point 362. The point 362 of the needle 360, like the point 182 of the needle 180, is disposed only partially into the flexible wall 330 in a storage state, with the actuator 306 causing the point 362 to move between the storage state and a delivery state wherein the point 362 is disposed through the interior surface 332 of the flexible wall 330 into the sterile reservoir 340. The container needle 360 may be in fluid communication with a injection needle 370 having a point 372 covered with a shield 374 through a cannula 380 received within a piston rod 382, for example, which rod 382 may be used to move the stopper/piston 330 between the ends 320, 322 of the container 302.

FIG. 6 shows a closely related variant to that illustrated in FIG. 5. According to the variant illustrated in FIG. 6, a container has a wall 390 with interior and exterior surfaces 392, 394. However, unlike the containers discussed previously, the wall 390 defines a closed end 396 and an open end 398. The container also includes a flexible wall 400, like the wall 330 of the embodiment of FIG. 5, which wall 400 is moveable within the container between the open end 398 and the closed end 396. According to this embodiment, a separate structure is not required to close off one of the ends 396, 398 because the wall 390 already defines the closed end 396 itself. For that matter, the closed end 396 may be resized so that it is radially larger than illustrated in FIG. 6.

Having thus discussed a plurality of embodiments wherein a seal assembly includes only a flexible unitary wall, a further plurality of embodiments will be discussed with reference to FIGS. 7-11 wherein the seal assembly includes a plurality of walls and/or seals. This structure may also be referred to as a compartmentalized seal (or septum with reference to FIG. 7, or stopper with reference to FIGS. 8-11).

Figure 7:
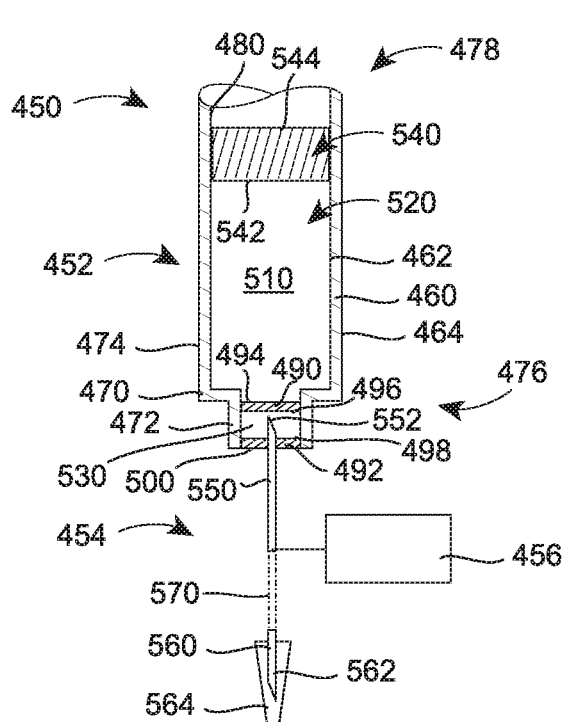
FIG. 7 is a cross-sectional view of an embodiment of an injector according to the present disclosure, with a rigid container needle in a storage state wherein the needle partially penetrates a clean barrier, but not a flexible wall, of a seal assembly.

Referring first to FIG. 7, an injector 450 includes a container 452, a fluid delivery system 454, and an actuator 456.

The container 452 includes a wall 460 with an interior surface 462 and an exterior surface 464. Like the container of FIGS. 1 and 2, the wall 460 may have a generally cylindrical shape, with a shoulder 470 separating a first cylindrical section 472 having a first cross-sectional diameter from a second cylindrical section 474 having a second cross-sectional diameter, the first cross-sectional diameter being smaller than the second cross-sectional diameter. The wall 460 may also define two opposed, open ends 476, 478. The wall 460, or more particularly the interior surface 462 of the wall 460, may also define a bore 480.

Unlike the container 102 of FIGS. 1 and 3, the container 452 of FIG. 7 has a seal assembly that includes more than a single, unitary wall. The seal assembly of the container 452 includes a flexible wall 490 and a clean barrier 492. The flexible wall 490 has an interior surface 494 and an exterior surface 496, while the clean barrier 492 has an interior surface 498 and an exterior surface 500. The interior surfaces 462, 494 of the wall 460 and the flexible wall 490 defining a closed sterile reservoir 510 filled with a drug product 520. On the other hand, the clean barrier 492 is disposed exterior of the flexible wall 490 to define an enclosed clean space 530 between the flexible wall 490 and the clean barrier 492. The clean space 530 may be defined by the interior surface 462 of the wall 460, the exterior surface 496 of the flexible wall 490, and the interior surface 498 of the clean barrier 492.

As illustrates, the container 452 may also include a stopper or piston 540 with interior and exterior surfaces 542, 544. The piston 540 may be received within the end 478 defined by the wall 460, and may be moveable along the bore 480 between the ends 476, 478 of the container 452. According to such an embodiment, the reservoir 510 within which the drug product 520 is disposed may be defined by the interior surfaces 462, 494, 542 of the walls 460, 490 and piston 540.

The embodiment of FIG. 7 also includes the fluid delivery system 454 comprising a clean, unsheathed, rigid container needle 550 having a point 552 disposed through the clean barrier 492 into the clean space 530 in a storage state, and disposed through the interior surface 494 of the flexible wall 490 into the sterile reservoir 510 in a delivery state. In this sense, the container needle 550 only partially penetrates the seal assembly. The fluid delivery system 454 may also include an injection needle 560 with a point 562 covered at least initially with a needle shield 564 to prevent contact with and contamination of the point 562. The container needle 550 and the injection needle 560 may be connected by a cannula or tube 570, which may be a flexible cannula according to certain embodiments of the present disclosure.

As was the case with the embodiment of FIGS. 1 and 3, the present disclosure includes a number of variants for the embodiment illustrated in FIG. 7, which variants are illustrated in FIGS. 8-11.

Figure 8:
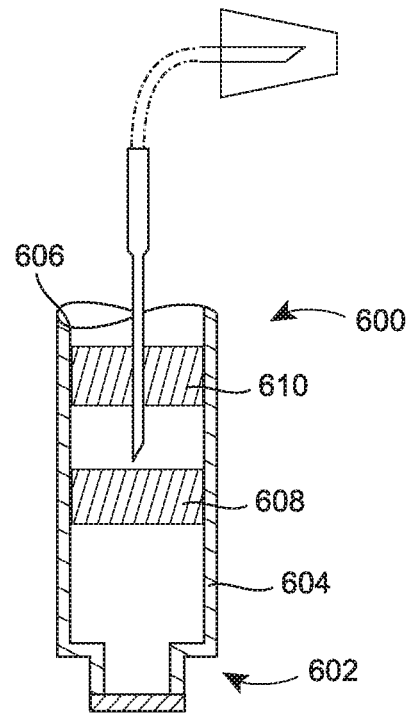
FIG. 8 is a cross-sectional view of an alternative embodiment of an injector according to the present disclosure, with a rigid container needle in a storage state wherein the needle partially penetrates a clean barrier, but not a flexible wall, of a seal assembly.

The embodiment of FIG. 8 is similar to the embodiment of FIG. 7 in the way that the embodiment of FIG. 5 was similar to that of FIGS. 1 and 3. In particular, the seal assembly of an injector 600 according to the embodiment of FIG. 8 is disposed in a container 602 in place of the stopper/piston 540 illustrated relative to the container 452. That is, the container 602 includes a wall 604 that defines a bore 606, and a flexible wall 608 and a clean barrier 610 each define a stopper that is moveable along the bore 606. While the wall 604 of the container 602 does not define opposing open and closed ends in the embodiment illustrated, such an alternative is possible according to the present disclosure similar to FIG. 6.

Figure 9:
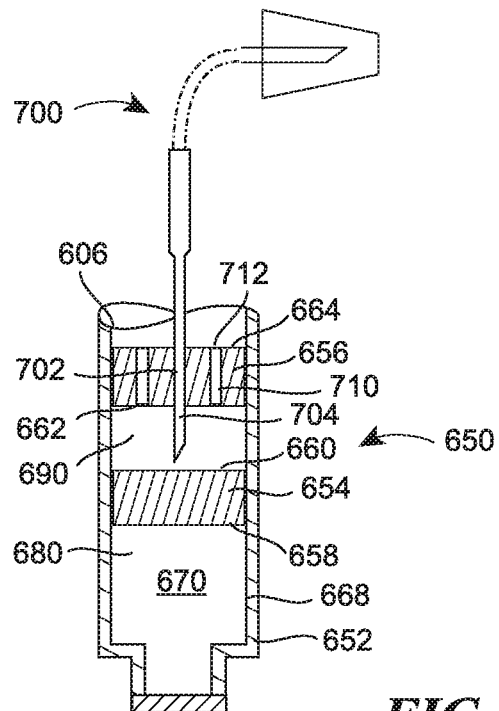
FIG. 9 is a cross-sectional view of a variant to the embodiment of FIG. 8 including vents to evacuate a clean space between a flexible wall and an exteriorly disposed clean barrier as an associated container needle is moved between a storage state and a delivery state.

FIGS. 9-11 illustrate variants to the embodiment illustrated in FIG. 8, which variants include additional features to permit the space or region between the flexible wall and the clean barrier to be evacuated or exhausted. These additional features may be referred to as vents, valves or bypasses, but all of these structures permit gases to escape from the space or region between the flexible wall and the clean barrier when an actuator moves the associated container needle from a storage state to a delivery state. This is not to suggest that the inner wall and exterior barrier cannot remain separated, for example through the use of a spacer or spacers, according to other embodiments of the present disclosure. However, the alternatives of FIGS. 9-11 illustrate options for evacuating the clean space as to those embodiments where the inner wall and exterior barrier come together.

A container 650 is illustrated in FIG. 9 including a wall 652 and a seal assembly, the assembly including a flexible wall 654 and a clean barrier 656. The flexible wall 654 has an interior surface 658 and an exterior surface 660, while the clean barrier 656 has an interior surface 662 and an exterior surface 664. An interior surface 668 of the wall 652 and the interior surface 658 of the flexible wall 654 defining a closed sterile reservoir 670 filled with a drug product 680. On the other hand, the clean barrier 656 is disposed exterior of the flexible wall 654 to define an enclosed clean space 690 between the flexible wall 654 and the clean barrier 656. The clean space 690 may be defined by the interior surface 668 of the wall 652, the exterior surface 660 of the flexible wall 652, and the interior surface 662 of the clean barrier 656.

As is also illustrated in FIG. 10, a fluid delivery system 700 including a container needle 702 is used in conjunction with the seal assembly. The container needle 702 is illustrated in the storage state, wherein the container needle 702 is disposed through the clean barrier 656 so that a point 704 of the needle 702 is disposed in the clean space 690. The point 704 will penetrate the flexible wall 654 and depend into the reservoir 670 in a delivery state, not shown. It will be recognized that the needle 702 is not drawn to scale particularly as to its length, as is true of other embodiments illustrated here.

In contrast with the previously discussed embodiments, the container 650 illustrated in FIG. 9 includes at least one vent 710. The vents 710 are in fluid communication with the clean space 690 between the clean barrier 656 and the flexible wall 654. The vents 710 are selectively actuated to permit gas trapped between the clean barrier 656 and the flexible wall 654 to escape through the vents 710 when the seal assembly is moved between the illustrated storage state and the delivery state, wherein the clean barrier 656 is advanced in the direction of the flexible wall 654 to permit the point 704 of the container needle 702 to penetrate through the wall 654. However, the vents 710 may be in a sealed condition relative to the environment until actuated, for example, by a change in the pressure within the clean space 690.

As illustrated, the vents 710 are disposed within the clean barrier 656, and extend between the interior surface 662 and the exterior surface 664 of the barrier 656. A flap 712 covers the end of the vent 710 proximate to the exterior surface 664, and thereby seals the end of the vent 710 until the vent is actuated, preserving the cleanliness of the space 690 between the clean barrier 656 and the flexible wall 654. Alternatively, the vents 710 may be arranged, for example, in the wall 652 of the container 650.

FIGS. 10 and 11 illustrate a further variant on the system of FIG. 8, wherein a container 720 includes a wall 722 and a seal assembly, the assembly including a flexible wall 724 and a clean barrier 726. The flexible wall 724 has an interior surface 728 and an exterior surface 730, while the clean barrier 726 has an interior surface 732 and an exterior surface 734. An interior surface 738 of the wall 722 and the interior surface 728 of the flexible wall 724 define a closed sterile reservoir 740 filled with a drug product 750. On the other hand, the clean barrier 726 is disposed exterior of the flexible wall 724 to define an enclosed clean space 760 between the flexible wall 724 and the clean barrier 726. The clean space 760 may be defined by the interior surface 738 of the wall 722, the exterior surface 730 of the flexible wall 724, and the interior surface 732 of the clean barrier 726.

As is also illustrated in FIG. 10, a fluid delivery system 770 including a container needle 772 is used in conjunction with the seal assembly. The container needle 772 is illustrated in the storage state, wherein the container needle 772 is disposed through the clean barrier 726 so that a point 774 of the needle 772 is disposed in the clean space 760. The point 774 will penetrate the flexible wall 724 and depend into the reservoir 740 in a delivery state, not shown.

In contrast with the previously discussed embodiments, the container 720 illustrated in FIG. 10 includes at least one bypass or vent 780. The bypasses 780 are in fluid communication with the reservoir 740. The bypasses 780 are selectively actuated to permit gas trapped between the clean barrier 726 and the flexible wall 724 to escape through the bypasses 780 into the reservoir 740 when the seal assembly is moved between the illustrated storage state and the delivery state, wherein the clean barrier 726 is advanced in the direction of the flexible wall 724 to permit the point 774 of the container needle 772 to penetrate through the wall 724.

However, the bypasses 780 are not in fluid communication with the clean space 760 until the flexible wall 724 has moved from the storage state illustrated in FIG. 10 to an intermediate state illustrated in FIG. 11. As illustrated in FIGS. 10 and 11, the bypasses 780 may be defined in the interior surface 738 of the wall 722, and as illustrated may take the form of a groove 782 formed in the wall 722. The groove 782 may have a distal end 784 and a proximal end 786. As will be recognized, until the exterior surface 730 of the flexible wall 724 moves past the distal end 784 of the grooves 782, the reservoir 740 is in a sealed condition relative to the clean space 760. However, once the exterior surface 730 of the flexible wall 724 moves past distal end 784 of the grooves 782, the gases trapped between the clean barrier 726 and the flexible wall 724 may exhaust into the reservoir 740. This may facilitate the movement of the barrier 726 and needle 772 toward the flexible wall 724.

While all of the forgoing embodiments have focused to one degree or another on a fluid delivery system partially disposed through a seal assembly, there are other alternatives where the container needle is not disposed through the seal assembly, or where the container needle is disposed fully through the seal assembly. Three such alternatives are illustrated in FIGS. 12-14.

FIG. 12 illustrates an injector 800 with a container 802, a fluid delivery system 804 and an actuator 806. Similar to the embodiments illustrated above, the actuator 806 would cause the fluid delivery system 804 to be disposed through a seal assembly associated with the container 802 in a delivery state, and thereby be in fluid communication with the interior of the container 802. However, as mentioned above, in the storage state illustrated in FIG. 12, the fluid delivery system is not even partially disposed through the seal assembly.

To this end, the container 802 includes at least a flexible wall 810, which may be in the form of a septum or a stopper according to the present disclosure. The flexible wall 810 has an interior surface 812 and an exterior surface 814. Additionally, the fluid delivery system 804 includes a container needle 816, an injection needle 818, and a flexible conduit 820 connecting the container needle 816 and the injection needle 818. Both the container needle 816 and the injection needle 818 are received within a cover 822, 824 that preserves the cleanliness of the needle 816, 818. The cover 822 may be referred to as a cap, while the cover 824 may be referred to as a shield. Also included is an alcohol wipe 826 disposed between the flexible wall 810 and the cover 822, which wipe 826 may be kept in an air-tight condition to maintain alcohol saturation.

According to the present disclosure, prior to initiating action of the actuator 806, the wipe 826 is drawn out from between the flexible wall 810 and the cover 822. For example, an end of the wipe 826 may be disposed outside housing of the injector 800 to permit the end to be grasped and the wipe 826 pulled out from the injector 800. Alternatively, the end of the wipe 826 may be attached to another aspect of the injector 800, such as a liner that covers an adhesive surface of the injector 800 that will be attached to the patient, such that when the liner is removed to expose the adhesive surface, the wipe 826 is pulled out from the injector 800 as well. The removal of the wipe sterilizes surface 814 of the wall 810 and opposing surface 828 of the cap 822. The actuator 806 then moves the container needle 816 through the cap 822 and the flexible wall 810.

FIGS. 13 and 14, on the other hand, illustrated embodiments wherein the container needle is disposed through the flexible wall (defining the stopper or septum) and a valve is used to seal the reservoir off from the injection needle. The valve may also be used to control the flow of drug product from the reservoir in the container. In this fashion, the valve may be used to meter an amount of drug product from the reservoir, or to delay the flow of the drug product until a time delay has elapsed relative to receipt of an input from an input device (e.g., button or switch), for example.

As such, FIG. 13 illustrates an injector 850 with a container 852, a fluid delivery system 854 and an actuator 856. The container 852 includes at least a flexible wall 860, which may be in the form of a septum according to the illustrated embodiment. The flexible wall 860 has an interior surface 862 and an exterior surface 864. Additionally, the fluid delivery system 854 includes a container needle 866, an injection needle 868, and a flexible cannula or tubing 870 connecting the container needle 866 and the injection needle 868. The injection needle 868 may be received within a cover 872 that preserves the cleanliness of the needle 868.

On the other hand, the container needle 866 (and in particular a point 874 of the container needle 866) is disposed through the flexible wall 860 through the interior surface 862. The needle 866 is thus in fluid communication with a sterile reservoir 880 and a drug product 890 disposed within the reservoir 880. Fluid communication between the container needle 866 and the injection needle 868 is interrupted by a valve 900 disposed in or along the flexible tubing 870, which valve 900 may define a boundary between the sterile portion of the injector 850 and the clean portion of the injector 850. Thus, unlike the other embodiments discussed above relative to FIGS. 1-12, the actuator 856 of the injector 850 is not used to move the container needle 866 relative to the flexible wall 860, but instead to manipulate the valve between a closed state wherein fluid communication is interrupted between the needles 866, 868 and an open state wherein the container needle 866 is in fluid communication with the injection needle 868.

It will be recognized that the valve 900 may take a variety of shapes and forms, two of which are illustrated in FIGS. 13 and 14. In particular, FIG. 13 illustrates an embodiment of the injector 850 wherein a rotatable valve 900 is disposed in the flexible tubing 870, or has an internal valve member that is in fluid communication with the fluid flow path defined between the container needle 866 and the injection needle 868. FIG. 14, by contrast, illustrates an embodiment of the injector wherein a pinch valve 902 is disposed along the flexible tubing 870, and thus cooperates with an exterior surface of the tubing 870 to interrupt the fluid communication between the container needle 866 and the injection needle 868.

Embodiments such as are illustrated in FIGS. 13 and 14 would also work well with a container that has a permanently attached needle, such that the container is in the form of a syringe, for example.

It will be further understood that the embodiments illustrated in FIGS. 13 and 14 may be further modified to incorporate a seal assembly including a plurality of walls and/or seals, such as is illustrated in FIG. 7, for example. FIG. 15 illustrates such an embodiment.

In particular, FIG. 15 illustrates an injector 920 with a container 922, a fluid delivery system 924, an actuator 926, and a seal assembly 928. The fluid delivery system 924 may include a container needle 930, an injection needle 932, and a flexible cannula or tubing 934 connecting the container needle 930 and the injection needle 932. The injection needle 932 may be received within a cover 936 that preserves the cleanliness of the needle 932. The needle 932 may also be in selective fluid communication with a sterile reservoir 940 and a drug product 942 disposed within the reservoir 940 via a valve 944 disposed in or along the flexible tubing 934. In this regard, the injector 920 is similar to those illustrated in FIGS. 13 and 14.

However, the seal assembly 928 of the injector 920 also has a flexible wall 950 and a clean barrier 952. The flexible wall 950 and the clean barrier 952 each have interior and exterior surfaces, with the interior surface of the flexible wall 950 defining, in part, the closed sterile reservoir 940. On the other hand, the clean barrier 952 is disposed exterior of the flexible wall 950 to define an enclosed clean space 954 between the flexible wall 950 and the clean barrier 952 in which a point 956 of the container needle 930 may be disposed.

In this regard, the embodiment of FIG. 15 has two potential barriers: one in the form of the valve 944 and a second in the form of the placement of the point 956 within the clean space 954. In fact, the valve 944 may be controlled to provide a delay in the injection of the drug product 942 after the container needle 930 has been caused to penetrate trough the flexible wall 950 into the reservoir 940.

As will be recognized, the devices according to the present disclosure may have one or more advantages relative to conventional technology, any one or more of which may be present in a particular embodiment in accordance with the features of the present disclosure included in that embodiment. As one example, these embodiments maintain the sterility of the drug product until the time of use. As another example, the potential for mixing of the drug product is limited or eliminated prior to the time of use. As a still further example, unintended delivery of the drug product is limited or prevented prior to the time of use.

Figure 16:
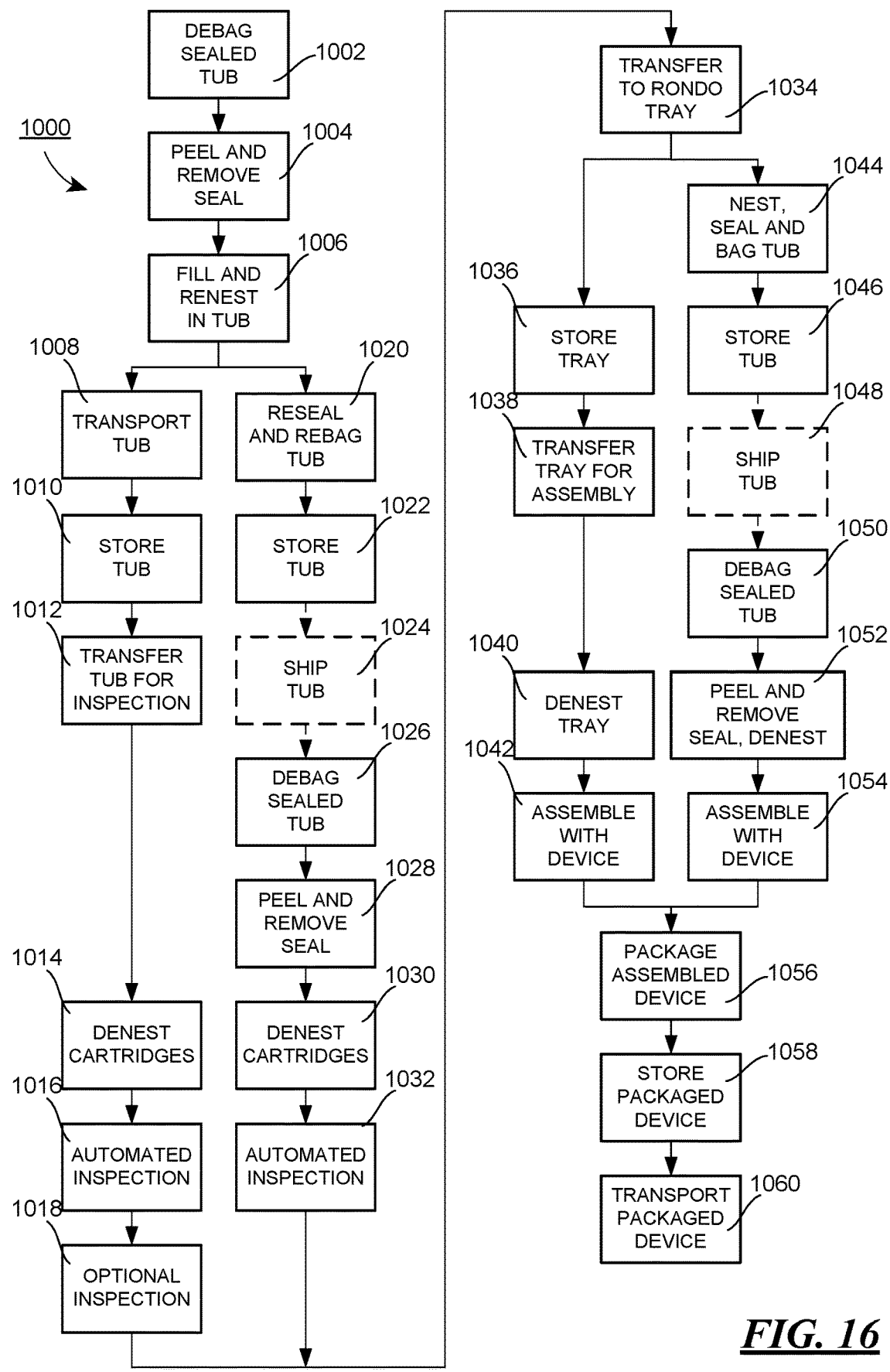
FIG. 16 is a flowchart illustrating a method of assembling an injector according to the present disclosure.

For illustrative purposes only, FIG. 16 provides a further method 1000 for assembling delivery devices according to any of the embodiments disclosed above. The method 1000 follows the general processing flow outlined above relative to FIG. 4. However, rather than referring to the cleanroom classifications according to U.S. Federal Standard 209E, reference is made to cleanroom classifications according to the GMP EU standard. Moreover, the method 1000 provides additional optional paths (represented as a left or right branch) that may be followed in the assembly of the delivery device. Consequently, the method 1000 of FIG. 16 may be viewed as supplementary to the discussion above relative to FIG. 4.

The method 1000 for assembling delivery devices begins at block 1002. The containers used in the device are initially stored in sealed tubs. As mentioned above, these containers may be or may have been sterilized at some point. At block 1002, the tubs are debagged, for example using an automated debagger in a Grade C cleanroom. At block 1004, the Tyvek seal is peeled off (e.g., by a robot) and removed, for example, in a space operated as a Grade A cleanroom, perhaps within an isolator in a space otherwise operated a Grade C cleanroom.

The containers are filled and stoppers are attached, and then the containers are re-nested in open tubs, at block 1006, in a space operated as a Grade A cleanroom, perhaps within an isolator in a space otherwise operated a Grade C cleanroom. From this point, two different alternative paths, or branches, are possible.

The filled containers may be left in the open tubs at block 1008. The tubs may be conveyed and carted to a storage space (e.g., cold room) at block 1010.

If the route of block 1008, 1010 is followed, then the method 1000 may continue with the tubs being transferred for processing to an inspection room at block 1012. The filled containers are then denested from the open tubs at block 1014, and supplied to an automated inspection machine at block 1016. Automated inspection of the filled containers occurs at block 1016, followed by optional, additional semi-automated or manual inspection at block 1018.

Alternatively, the tubs may be resealed, rebagged, and labeled, at block 1020. For example, the tubs may be resealed with Tyvek (e.g., using a Bausch+Strobel tub sealer), rebagged, and then labeled in a Grade C cleanroom at block 1020. The tubs may then be stored, or even shipped, if necessary, at blocks 1022, 1024.

Once storage or transport is completed, the tubs are debagged, for example using an automated debagger at block 1026. At block 1028, the Tyvek seal is peeled off and removed. The filled containers may then be denested for inspection, at block 1030. The actions at blocks 1026, 1028, 1030 are performed in a Grade C cleanroom. An automated inspection may then be carried out using a visual inspection machine designed for operation in a Grade C cleanroom at block 1032.

Following either procedure, the filled, inspected containers may then be transferred to rondo trays at block 1034.

According to a first procedure, the rondo trays may be sent directly to storage at block 1036. If the route of block 1036 is followed, then the rondo trays are transferred for processing to the device assembly room at block 1038. The containers are denested at block 1040, and assembled with the other elements of the delivery device at block 1042 to define an assembled delivery device (e.g., an injector or an infuser).

Alternatively, the containers may be moved into tubs, which are sealed, bagged, and labeled, at block 1044. For example, the tubs may be resealed with Tyvek, bagged, and then labeled in a Grade C cleanroom. The tubs may then be stored, or even shipped for further processing, if necessary, at blocks 1046, 1048. Once storage or transport completed, the tubs are debagged, for example using an automated debagger at block 1050. At block 1052, the Tyvek seal is peeled off and removed, and the containers are denested. The filled containers may then be assembled with the other elements of the delivery device at block 1054. The actions at blocks 1050, 1052, 1054 may all occur in a Grade C cleanroom.

In either event, the assembled devices are packaged at block 1056, and the packaged, assembled devices are stored at block 1058. Finally, the packaged, assembled devices are transported to the distributor, and/or for other distribution actions at block 1060.

Other advantages not specifically listed herein may also be recognized as well. Moreover, still other variants and alternatives are possible.

As an example, while the operation of the actuator has been described in regard to the foregoing embodiments as moving, for example, the container needle from a storage state to a delivery state, it will be understood that the actuator may also move the container needle from the delivery state to the storage state. For example, if a dose of drug product is to be delivered that is less than the volume of the reservoir (such as may be the case wherein the injector is designed to be programmed to deliver an adjustable dose according to the needs of the patient (e.g., pediatric vs. adult patient)), then the actuator may move the container needle from the storage state to the delivery state prior to delivery of the dose, and from the delivery state to the storage state after delivery of the dose. The movement from the delivery state to the storage state will in effect reseal the container and close the fluid path to the patient. This sequence of movement between the storage state and the delivery state may be repeated. As noted above, maintaining a closed fluid path until delivery is initiated is advantageous in that the opportunity for unintended delivery of the drug product to the patient and/or mixing of the drug product with the patient's bodily fluids is reduced.

The injectors according to the present disclosure may be used with a variety of drug products, including colony stimulating factors, such as granulocyte colony-stimulating factor (G-CSF), may be administered to increase the number of immune cells (e.g., white blood cells) found in bone marrow or peripheral blood. Such G-CSF agents include, but are not limited to, Neupogen® (filgrastim) and Neulasta® (pegfilgrastim).

In other embodiments, the injector may be used with various other products including, for example, an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/

0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

PCSK9 (Proprotein Convertase Subtilisin/Kexin) specific antibodies, peptibodies, related proteins and the like including but not limited to those described in U.S. Pat. No. 8,030,457, WO 11/0027287 and WO 09/026558, which are herein incorporated by reference in their entirety, particularly in parts pertinent to proteins that bind PCSK9;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/068,289, which is incorporated herein by reference in its entirety, particularly in parts pertinent to proteins that bind OX40L and/or other ligands of the OX040 receptor; and Other exemplary proteins can include Activase® (alteplase, tPA); Aranesp® (darbepoetin alfa); Epogen®

(epoetin alfa, or erythropoietin); Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

We claim:

1. An injector comprising:
    a container including a first wall with an interior surface and a septum with an interior surface, the interior surfaces of the first wall and the septum at least partially defining a reservoir, wherein the septum is fixed with respect to the first wall of the container;
    a stopper movably disposed in the container;
    a needle having at least a first position and a second position; and
    a second wall positioned exterior to the septum such that the septum and the second wall at least partially define an enclosed space disposed between the septum and the second wall, wherein a point of the needle is disposed adjacent to the second wall in the first position and disposed through the septum in the second position,
    wherein the needle and the second wall are configured such that the needle moves with respect to the second wall in moving from the first position to the second position.

2. The injector of claim 1, wherein the second wall is free from contact with the septum.

3. The injector of claim 1, wherein the second wall is immovable with respect to the first wall of the container.

4. The injector of claim 1, wherein the second wall is coupled with the needle such that the point of the needle penetrates the second wall in the first position.

5. The injector of claim 1, comprising an actuator configured to move the needle from the first position to the second position.

6. The injector of claim 5, comprising a mechanical input device coupled to the actuator.

7. The injector of claim 5, comprising an electrical or electro-mechanical input device coupled to the actuator.

8. The injector of claim 1, wherein the septum comprises a flexible unitary wall.

9. The injector of claim 1, comprising:
    an injection needle for insertion into a patient; and
    a flexible tubing connecting the needle and the injection needle.

10. The injector of claim 1, wherein the second wall comprises a second septum and the needle is disposed through the second septum in the second position.

11. The injector of claim 1, wherein the injector is manufactured with the point of the needle disposed in the enclosed space in the first position.

12. The injector of claim 1, wherein the point of the needle is disposed in the enclosed space prior to any user-initiated movement of the needle with respect to the container.

13. The injector of claim 1, wherein the injector is packaged with the point of the needle disposed in the enclosed space in the first position.

14. The injector of claim 1, wherein the point of the needle is initially, prior to use, disposed stationarily in the enclosed space in the first position.

15. The injector of claim 1, comprising a drug disposed in the container, the drug comprising at least one of: a granulocyte colony-stimulating factor, a pegylated granulocyte colony-stimulating factor, a PCSK9-specific antibody, an erythropoiesis stimulating agent, a TNF blocker, an interleukin-receptor specific antibody, an IGF-receptor specific antibody, or a TGF-specific antibody.

16. A method of assembling an injector, the method comprising:
    filling a reservoir of a container with a drug, the container including a first wall with an interior surface and a septum with an interior surface, the reservoir after filling being defined at least by the interior surface of the first wall of the container, and the interior surface of the septum of the container, wherein the septum is fixed with respect to the first wall of the container;
    providing a stopper movably disposed in the container;
    positioning a second wall exterior to the septum such that the septum and the second wall at least partially define an enclosed space disposed between the septum and the second wall; and
    positioning a point of a needle adjacent to the second wall to define a first position of the needle, the point of the needle being configured to be disposed through the septum in a second position of the needle, the needle and the second wall being configured such that the needle moves with respect to the second wall in moving from the first position to the second position.

17. The method of claim 16, wherein the second wall is free from contact with the septum.

18. The method of claim 16, wherein the second wall is immovable with respect to the first wall of the container.

19. The method of claim 16, wherein the second wall is coupled with the needle such that the point of the needle penetrates the second wall in the second position.

20. The method of claim 16, the drug comprising at least one of: a granulocyte colony-stimulating factor, a pegylated granulocyte colony-stimulating factor, a PCSK9-specific antibody, an erythropoiesis stimulating agent, a TNF blocker, an interleukin-receptor specific antibody, an IGF-receptor specific antibody, or a TGF-specific antibody.

* * * * *